(12) United States Patent
Dinger et al.

(10) Patent No.: US 6,610,066 B2
(45) Date of Patent: Aug. 26, 2003

(54) SUCTION RASP AND HANDPIECE ADAPTER ASSEMBLY AND POWERED SURGICAL HANDPIECE ASSEMBLY INCLUDING A SUCTION RASP

(75) Inventors: Fred B. Dinger, Jacksonville, FL (US); John T. Cleveland, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 106 days.

(21) Appl. No.: 09/846,221

(22) Filed: May 2, 2001

(65) Prior Publication Data

US 2001/0039427 A1 Nov. 8, 2001

Related U.S. Application Data

(62) Division of application No. 09/404,460, filed on Sep. 24, 1999, now Pat. No. 6,368,324.

(51) Int. Cl.[7] .............................. A61B 17/56
(52) U.S. Cl. .......................... 606/85; 604/22
(58) Field of Search .................. 606/84, 85, 83, 606/79; 604/22; 451/456; 600/571

(56) References Cited

U.S. PATENT DOCUMENTS

| | | |
|---|---|---|
| 1,866,529 A | 7/1932 | Farkas |
| 3,260,289 A | 7/1966 | Whitten |
| 3,678,934 A * | 7/1972 | Warfield et al. |
| 4,020,555 A | 5/1977 | Hedrick |
| 4,108,182 A | 8/1978 | Hartman et al. |
| 4,210,146 A | 7/1980 | Banko |
| 4,246,902 A | 1/1981 | Martinez |
| 4,700,702 A | 10/1987 | Nisson |
| 5,201,749 A | 4/1993 | Sachse et al. |
| 5,490,860 A | 2/1996 | Middle et al. |
| 5,540,693 A * | 7/1996 | Fisher ................ 606/79 |
| 5,707,374 A * | 1/1998 | Schmidt ............. 606/85 |
| 5,814,049 A * | 9/1998 | Pratt et al. ......... 606/80 |
| 5,833,643 A | 11/1998 | Ross et al. |

* cited by examiner

Primary Examiner—Michael H. Thaler

(57) ABSTRACT

A surgical handpiece adapter for converting rotary motion of a powered surgical handpiece into reciprocating motion to drive a cutting member includes a rear drive shaft for being removably coupled to a rotatable drive shaft of the handpiece, a front drive shaft for being removably coupled to the cutting member and a motion converting mechanism causing reciprocation of the front drive shaft and, therefore, the cutting member coupled thereto, in response to rotation of the rear drive shaft by the drive shaft of the handpiece. A handpiece adapter assembly is formed by an adapter and a cutting member coupled thereto, and a powered surgical handpiece assembly is formed by an adapter, a cutting member coupled to the adapter and a powered surgical handpiece coupled to the adapter. A cutting member includes a surgical suction rasp for being reciprocatively driven to cut anatomical tissue and having a tissue cutting surface and a suction passage with an inlet opening along the tissue cutting surface for removing anatomical debris from an operative site at which the rasp is used. A cutting member includes an osteotome for being reciprocatively power driven to cut anatomical tissue and having a cutting edge and a blunt tip extending distally of the cutting edge. A method of facial surgery includes the steps of reciprocating a distal end of a rasp to reshape the nasal bone of a patient and removing anatomical debris through a suction passage of the rasp while the nasal bone is being reshaped. Another method of facial surgery includes the steps of reciprocating a distal end of an osteotome via a powered surgical handpiece and moving the distal end of the osteotome, while it is being reciprocated, forwardly along the nasal bone of a patient in a predetermined path with a cutting edge of the osteotome in contact with the nasal bone to make a cut of desired length in the nasal bone along the predetermined path.

24 Claims, 7 Drawing Sheets

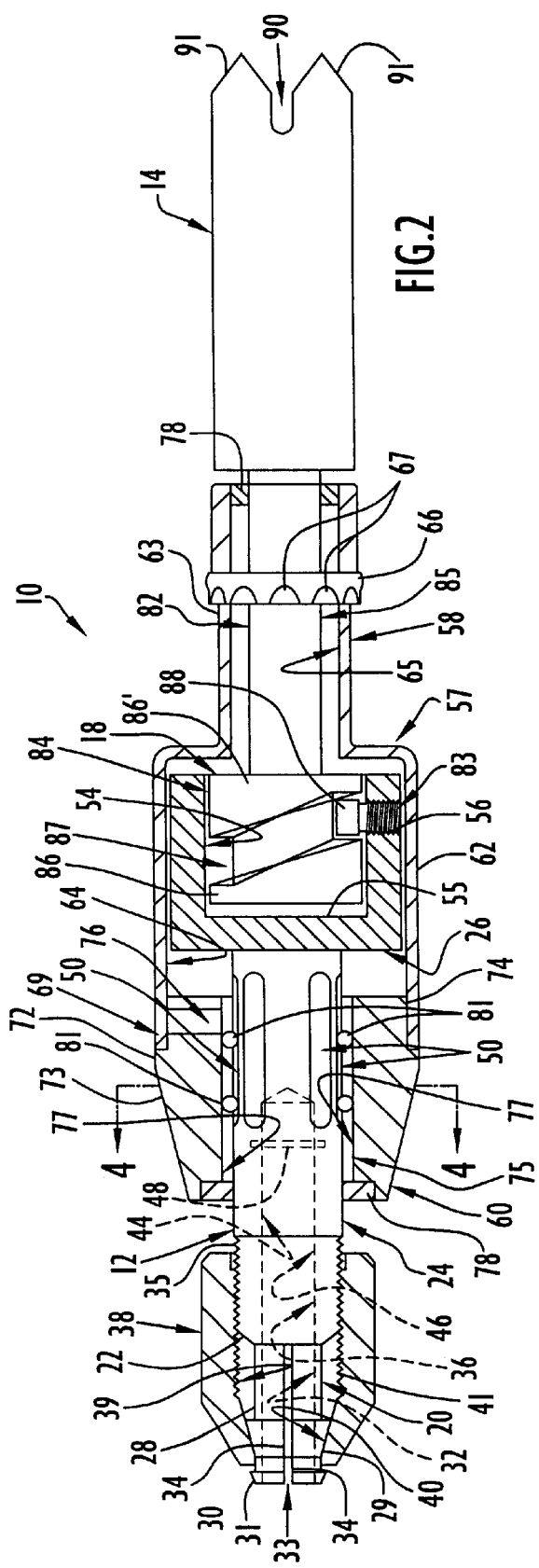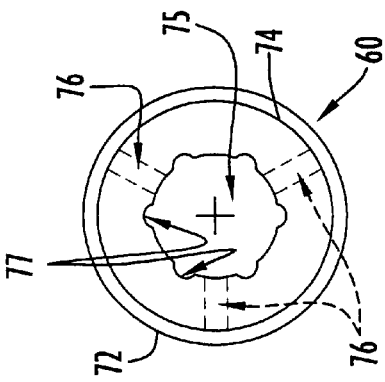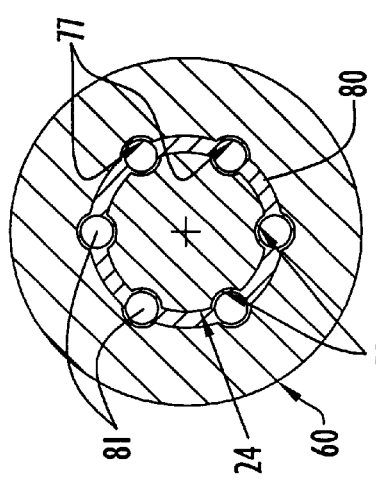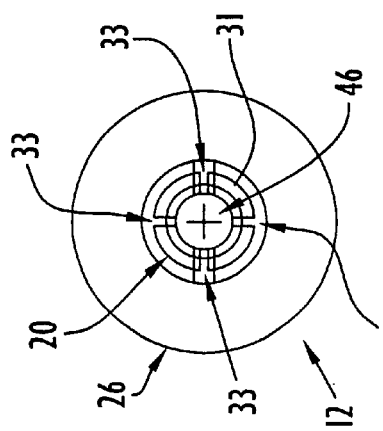

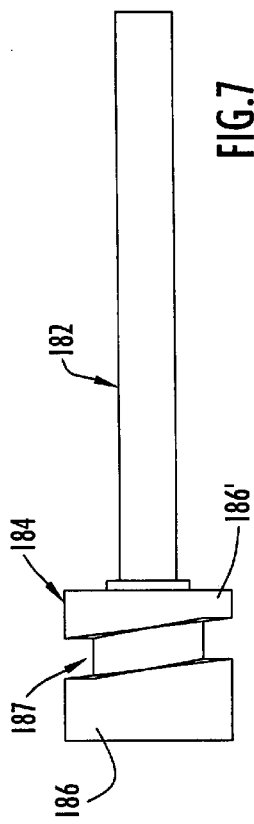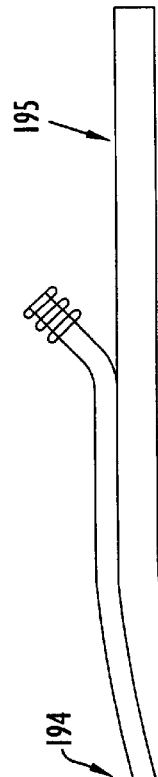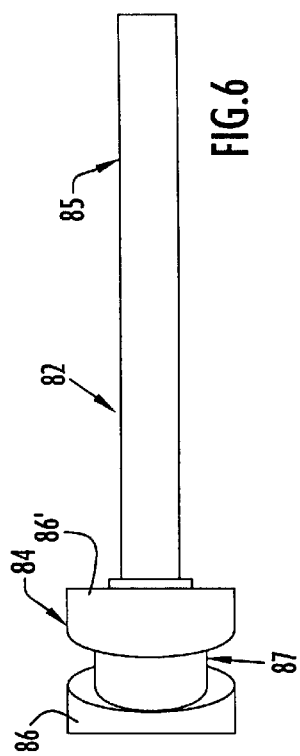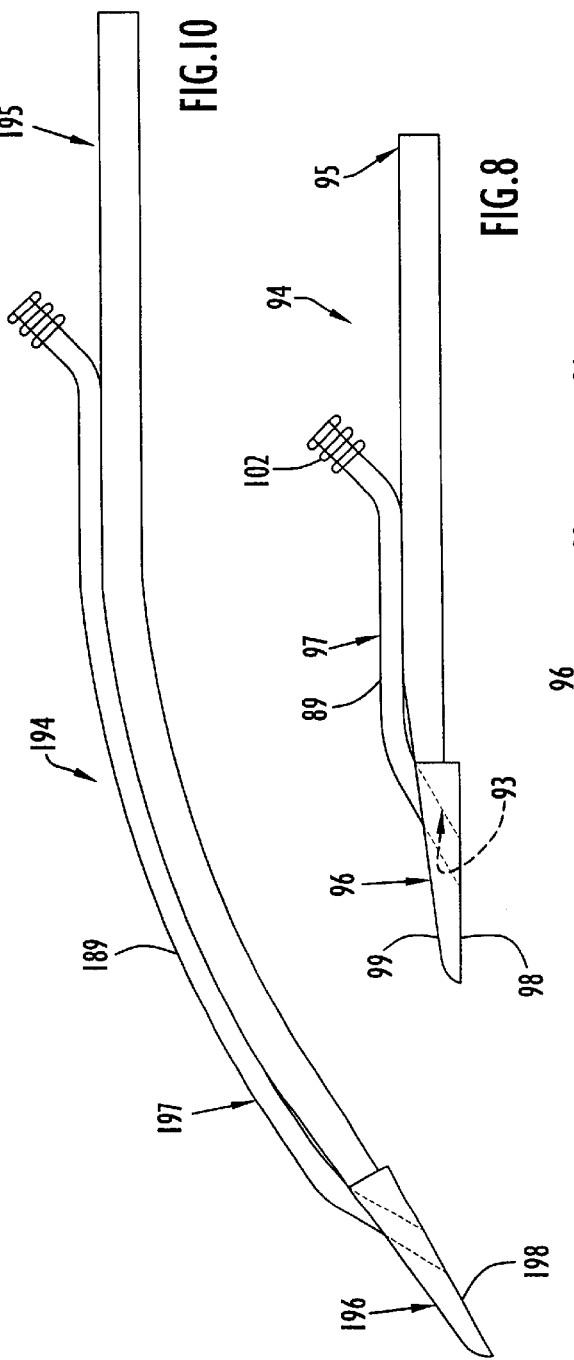

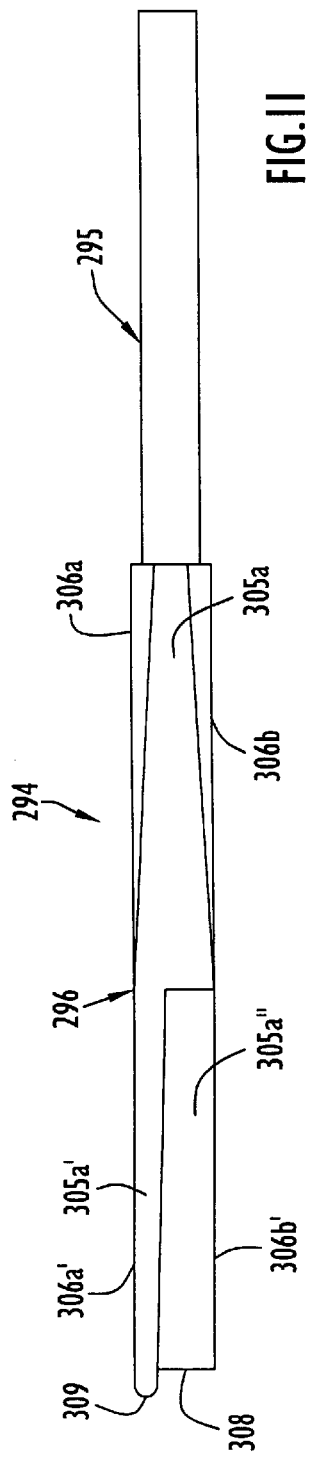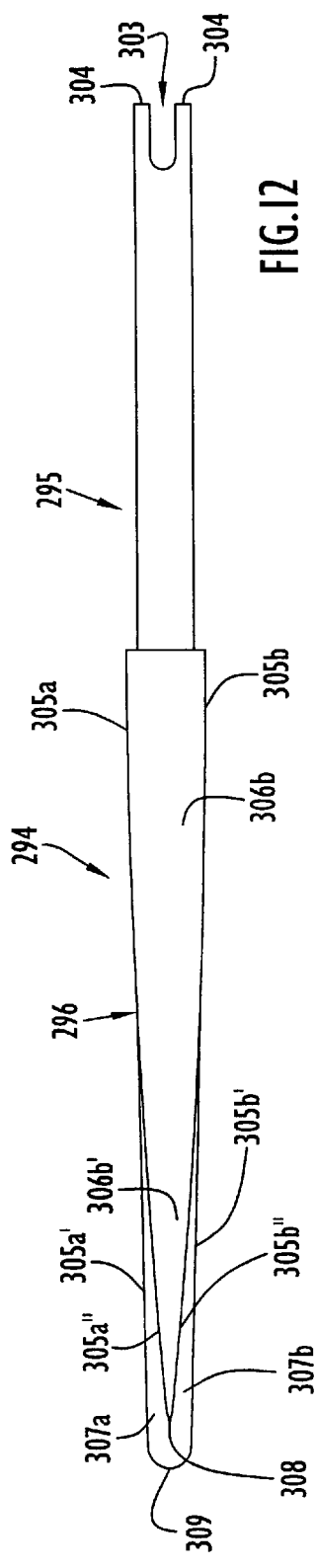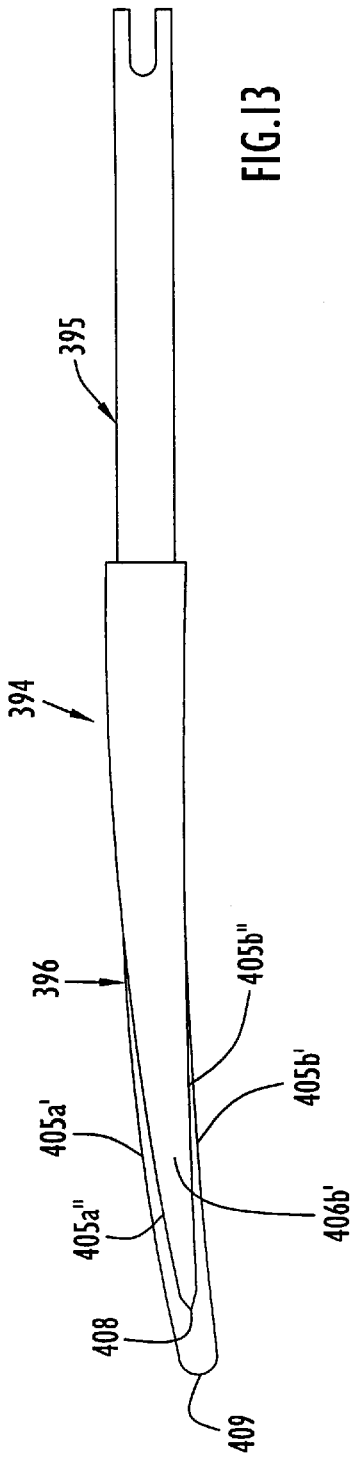

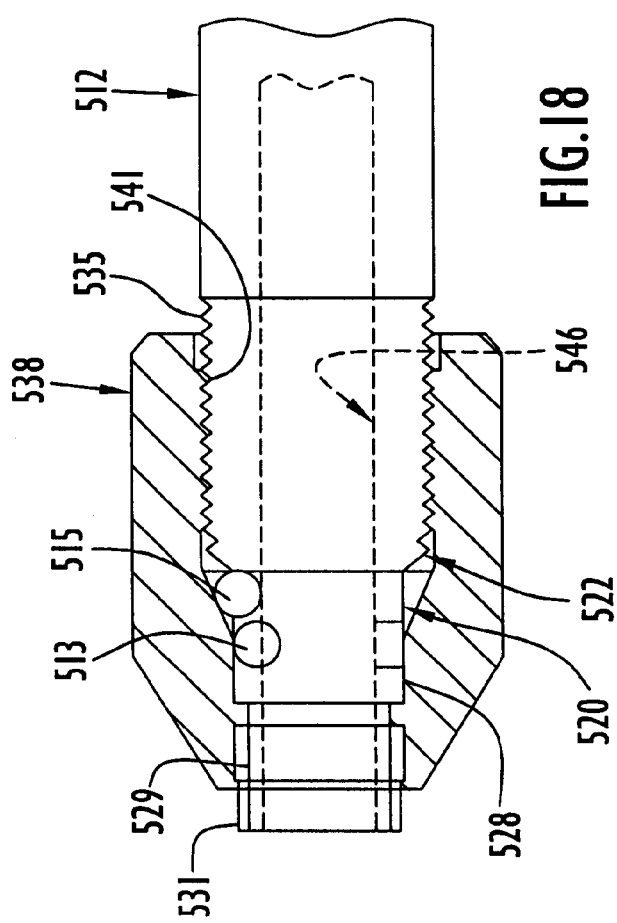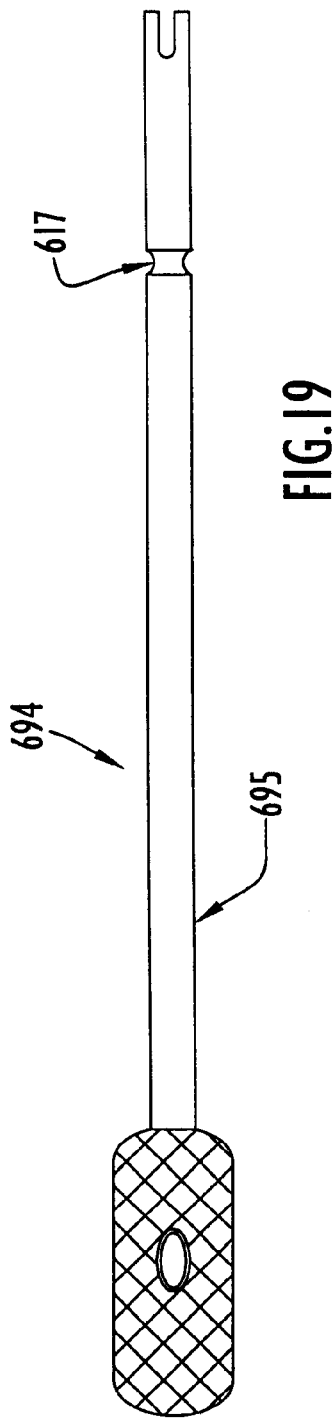

SUCTION RASP AND HANDPIECE ADAPTER ASSEMBLY AND POWERED SURGICAL HANDPIECE ASSEMBLY INCLUDING A SUCTION RASP

CROSS REFERENCE TO RELATED PATENT APPLICATIONS

This application is a divisional of prior U.S. patent application Ser. No. 09/404,460 filed Sep. 24, 1999, now U.S. Pat. No. 6,368,324 the disclosure of which is incorporated herein by reference. This application is related to prior patent applications Ser. No. 09/005,010, Ser. No. 09/005,012 and Ser. No. 09/005,014 filed Jan. 9, 1998, which are divisionals of prior application Ser. No. 08/775,147 filed Dec. 31, 1996 and now abandoned, and to Ser. No. 09/005, 189 filed Jan. 9,1998, which is a continuation of Ser. No. 08/775,147, which is a continuation-in-part of Ser. No. 08/719,130 filed Sep. 24, 1996 and now abandoned. The disclosures of all of the foregoing patent applications are incorporated herein by reference.

BACKGROUND OF THE INVENTION

1. Field of the Invention

The present invention generally relates to surgical handpiece adapters for powered surgical handpieces, to cutting members for being driven by surgical handpiece adapters, to powered surgical handpiece assemblies and to methods of facial surgery. More particularly, the present invention relates to a surgical handpiece adapter by which rotary motion of a powered surgical handpiece is converted to reciprocating motion, to cutting members for being reciprocatively driven by a rotary powered surgical handpiece via an adapter, to powered surgical handpiece assemblies incorporating a powered surgical handpiece, an adapter and a cutting member, to handpiece adapter assemblies incorporating an adapter and a cutting member and to methods of facial surgery using the same.

2. Brief Description of the Prior Art

Powered surgical handpieces are commonly used in many medical specialties to drive cutting members for performing various diverse cutting functions. One particularly advantageous reusable, powered or motorized surgical handpiece is the XPS™ StraightShot handpiece of Xomed, Inc., Jacksonville, Fla., the XPS™ StraightShot handpiece being the subject of prior patent applications Ser. No. 09/005,010, Ser. No. 09/005,012, Ser. No. 09/005,014 and Ser. No. 09/005,189, all of which were filed Jan. 9, 1998, Ser. No. 08/775,147 filed Dec. 31, 1996 and now abandoned and Ser. No. 08/719,130 filed Sep. 24, 1996 and now abandoned, the disclosures of all the foregoing patent applications being incorporated herein by reference. The XPS™ StraightShot handpiece has a front drive shaft rotatably driven by a motor of the handpiece. The front drive shaft has drive pins thereon for drivingly engaging prongs disposed on a proximal end of a blade or cutting member that is to be rotatably driven by the handpiece. The blade or cutting member is selectively engageable and disengeable with the front drive shaft allowing the handpiece to be used to rotatably drive a variety of blades or cutting members selectively coupled therewith. In accordance with the present invention, an adapter for the XPS™ StraightShot handpiece is provided by which the rotary motion of the front drive shaft is converted to reciprocating motion in order to reciprocatively drive a blade or cutting member.

Surgical cutting instruments wherein a rotatable output shaft of a motor, i.e. a driver, is used to reciprocate, via a cam and cam follower, a driven blade or cutting member have been proposed as exemplified by U.S. Pat. No. 4,108,182 to Hartman et al., U.S. Pat. No. 4,210,146 to Banco and U.S. Pat. No. 4,246,902 to Martinez. In prior surgical cutting instruments wherein rotary motion of the driver is converted to reciprocating motion of the driven blade or cutting member, the mechanism or structure by which the rotary motion is converted to the reciprocating motion is an integral, permanently installed part of the cutting instrument and cannot be detached or separated therefrom. Accordingly, such prior surgical cutting instruments, of which the foregoing patents are representative, can only be used to reciprocate a blade or cutting member and cannot also be used with blades or cutting members which are to be rotated.

Various other powered surgical handpieces having motors for driving removable blades or cutting members have also been proposed, as illustrated by the Stryker Hummer system of Stryker Endoscopy, San Diego, Calif., the Apex System of Linvatec, Incorporated, Largo, Fla., the PS 3500 and EP-1 Surgical Drive System of Dyonics, Inc. of Andover, Mass. and the Wizard microdebrider system of Xomed, Inc., Jacksonville, Fla. Such powered surgical handpieces are limited for use with blades or cutting members that are to be rotated and do not include any mechanism or structure by which the powered surgical handpieces can be adapted for use with blades or cutting members that are to be reciprocated.

In various surgical procedures, particularly in facial procedures including rhinoplasty and supraorbital reshaping, blades or cutting members such as rasps and/or osteotomes have been used to cut anatomical tissue such as bone. However, prior to the present invention, reciprocating rasps could not be used with the XPS™ StraightShot handpiece. In addition, prior reciprocating rasps do not have suction passages with inlet openings, respectively, disposed on tissue cutting surfaces, respectively, of the rasps, by which anatomical debris is withdrawn or removed from operative sites at which the rasps are used. Conventional osteotomes have been used in facial surgery to make medial and lateral cuts in the nasal bone of a patient during rhinoplasty. Conventional osteotomes are manually tapped into and/or along the nasal bone, via a mallet applied to proximal ends of the osteotomes, in order to make the required cuts. The latter process is tedious and time consuming, which places the patient at increased risk of complications. Furthermore, manual tapping in of conventional osteotomes is greatly subject to human error and increases the risk of unsatisfactory results, such that the results obtained with surgery are greatly dependent on the individual skill of the surgeon. Accordingly, it would be desirable to reciprocatively drive an osteotome with a powered surgical handpiece in order to enhance the quality of cuts made therewith, to reduce the time required to execute such cuts and to facilitate accomplishment of satisfactory results by surgeons of varying degrees of skill. It would also be desirable for various types of rasps and osteotomes to be reciprocated, via a removable adapter, by an XPS™ StraightShot handpiece which, when the adapter is removed therefrom, can also be used to rotatably drive rotatable blades or cutting members.

SUMMARY OF THE INVENTION

Accordingly, it is a primary object of the present invention to overcome the aforementioned limitations or disadvantages of prior powered surgical handpieces, rasps, osteotomes and methods of facial surgery.

Another object of the present invention is to adapt a powered surgical handpiece, having a rotatable driver, to reciprocatively drive a blade or cutting member removably coupled to the handpiece.

Yet another object of the present invention is to adapt the XPS™ StraightShot handpiece to reciprocatively drive a blade or cutting member.

A further object of the present invention is to provide a removable adapter for a powered surgical handpiece by which rotary motion of a drive shaft of the handpiece is converted to reciprocating motion, via the removable adapter, to reciprocatively drive a blade or cutting member removably coupled to the adapter.

A still further object of the present invention is to provide a removable adapter for the XPS™ StraightShot handpiece by which the handpiece is capable of being used to reciprocatively drive a blade or cutting member when the adapter is coupled with the handpiece and, when the adapter is removed from the handpiece, is capable of rotatably driving a blade or cutting member.

An additional object of the present invention is to provide a surgical rasp having a suction passage with an inlet opening on a tissue cutting surface of the rasp by which debris is withdrawn or removed from an operative site at which the rasp is used to cut anatomical tissue.

It is also an object of the present invention to reciprocatively drive a surgical rasp via the XPS™ StraightShot handpiece.

The present invention has as another object to reciprocatively drive an osteotome via a powered surgical handpiece.

Additionally, it is an object of the present invention to facilitate the performance of surgical facial procedures, particularly rhinoplasty and supraorbital procedures.

Some of the advantages of the present invention are that various reciprocatively moveable blades or cutting members can be used with a single adapter and handpiece, a single handpiece can be used to drive both rotatable and reciprocative blades or cutting members, various sizes of adapters can be provided in accordance with the strokes desired for the blades or cutting members and/or the forces exerted thereon by the blades or cutting members, the adapter can be designed with a particular stroke, a plurality of adapters can be provided with each adapter having a different stroke, a single handpiece can be used with various sizes of adapters, the handpiece and the adapters can be reusable while the blades or cutting members can be disposable for single patient use, the blades or cutting members can be reciprocated at various speeds in accordance with the speed selected for the motor of the handpiece, anatomical tissue can be cut by a rasp while simultaneously removing anatomical debris via a suction passage of the rasp, anatomical debris is removed from the operative site via the suction passage to a location external of the patient's body, the rasp can be designed with a curve or arc corresponding to the natural curvature of the human head from behind the eyebrow to the hairline for particularly advantageous use in supraorbital procedures, the tissue cutting surface of the rasp can be designed with various degrees of coarseness, the need for manually tapping in osteotomes during rhinoplasty is eliminated, the time required to cut bone during facial procedures is greatly reduced, the rasps and osteotomes can be used with various adapters and/or powered surgical handpieces, including conventional adapters and/or conventional powered surgical handpieces, and the rasps and osteotomes are particularly suited for use in minimally invasive surgical procedures.

These and other objects, advantages and benefits are achieved with the subject invention as generally categorized in a surgical handpiece adapter for converting rotary motion of a powered surgical handpiece into reciprocating motion for reciprocatively driving a blade or cutting member. The adapter includes a rear drive shaft having a proximal end for being removably coupled to a drive shaft of the handpiece and having a distal end, a front drive shaft having a distal end for being removably coupled to the cutting member and a motion converting mechanism by which rotation of the rear drive shaft by the drive shaft of the handpiece is converted to reciprocating motion of the front drive shaft and, therefore, the cutting member coupled therewith. The motion converting mechanism includes a cam at the distal end of the rear drive shaft and a cam follower on the front drive shaft in engagement with the cam. The cam causes reciprocation of the cam follower and, therefore, the front drive shaft, when the rear drive shaft is rotated.

A surgical handpiece adapter assembly is formed by the adapter and a cutting member coupled thereto. In one embodiment, the cutting member has a proximal end adapted to drivingly engage the distal end of the front drive shaft of the adapter when the cutting member is in a specific orientation relative to the adapter. In another embodiment, the cutting member has a groove for receiving a locking member of the adapter. A powered surgical handpiece assembly is formed by the adapter coupled to a powered surgical handpiece and to a cutting member. In one embodiment, the proximal end of the rear drive shaft of the adapter is adapted to drivingly engage the drive shaft of the handpiece when the cutting member is in a specific orientation relative to the handpiece, the specific orientation corresponding to the preferred orientation for use of the cutting member when the handpiece is manually grasped or held by a surgeon in the normal manner. Various types of cutting members, including rasps and osteotomes, may be used in a surgical handpiece adapter assembly and/or a powered surgical handpiece assembly incorporating the adapter of the present invention to be reciprocatively driven via the adapter to cut anatomical tissue including bone.

A surgical suction rasp according to the present invention includes an elongate member having a distal end and a proximal end, a tissue cutting surface at the distal end of the elongate member and a suction passage having an inlet along the tissue cutting surface and an outlet disposed proximally of the distal end of the elongate member. The proximal end of the rasp is adapted to be coupled with a drive shaft for reciprocating the distal end of the rasp to cut anatomical tissue with the tissue cutting surface while anatomical debris is removed through the suction passage. The rasp may be assembled to an adapter, such as the adapter of the present invention, to form a surgical handpiece adapter assembly. The rasp may be assembled to an adapter and to a powered surgical handpiece to form a powered surgical handpiece assembly.

Another surgical handpiece adapter assembly according to the present invention includes an osteotome coupled with an adapter capable of reciprocating the osteotome in response to the adapter being rotatably driven. Another powered surgical handpiece assembly according to the present invention includes an osteotome coupled with an adapter which, in turn, is coupled with a powered surgical handpiece. The adapter is capable of reciprocating the osteotome in response to the adapter being rotatably driven by the handpiece.

A method of facial surgery according to the present invention wherein the nasal bone of a patient is surgically reshaped includes the steps of introducing a distal end of a surgical suction rasp through an incision in the patient's nose, advancing the rasp along the nose to position the distal end at an operative site at which an area of the nasal bone is to be reshaped, positioning a tissue cutting surface at the distal end of the rasp in contact with the area of the nasal bone that is to be reshaped, reciprocating the distal end of the rasp to abrade and thusly reshape the nasal bone with the tissue cutting surface, and removing anatomical debris from the operative site through a suction passage of the rasp while the nasal bone is being reshaped.

A method of facial surgery according to the present invention wherein a cut is made in the nasal bone of a patient includes the steps of introducing a distal end of an osteotome through an incision in the patient's nose, positioning a cutting edge on the distal end of the osteotome at a location on the nasal bone at which a cut is to be made, reciprocating the distal end of the osteotome via a powered surgical handpiece, moving the distal end of the osteotome, while it is being reciprocated, forwardly along the bone in a predetermined path with the cutting edge in contact with the nasal bone to make a cut of desired length in the nasal bone along the predetermined path.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 2 is a side view, partly in section, of the surgical handpiece adapter according to the present invention.

FIG. 3 is a distal end view of a front drive shaft of the surgical handpiece adapter.

FIG. 4 is a sectional view taken along line 4—4 of FIG. 2.

FIG. 5 is a proximal end view of a distal housing member of the surgical handpiece adapter.

FIG. 6 is a top view of a cam of the surgical handpiece adapter.

FIG. 7 is a side view of an alternative cam for the surgical handpiece adapter.

FIG. 8 is a side view of a cutting member, which is a surgical suction rasp, according to the present invention.

FIG. 9 is a bottom view of the rasp of FIG. 8.

FIG. 10 is a side view of an alternative surgical suction rasp according to the present invention.

FIG. 11 is a side view of the cutting member, which is an osteotome, of FIG. 1.

FIG. 12 is a bottom view of the osteotome.

FIG. 13 is a bottom view of an alternative osteotome for use with the surgical handpiece adapter.

FIG. 18 is a broken side view, partly in section, of a distal portion of an alternative surgical handpiece adapter according to the present invention.

FIG. 19 is a bottom view of a further alternative rasp according to the present invention adapted for use with the adapter of FIG. 18.

DESCRIPTION OF THE PREFERRED EMBODIMENTS

Figure 1:
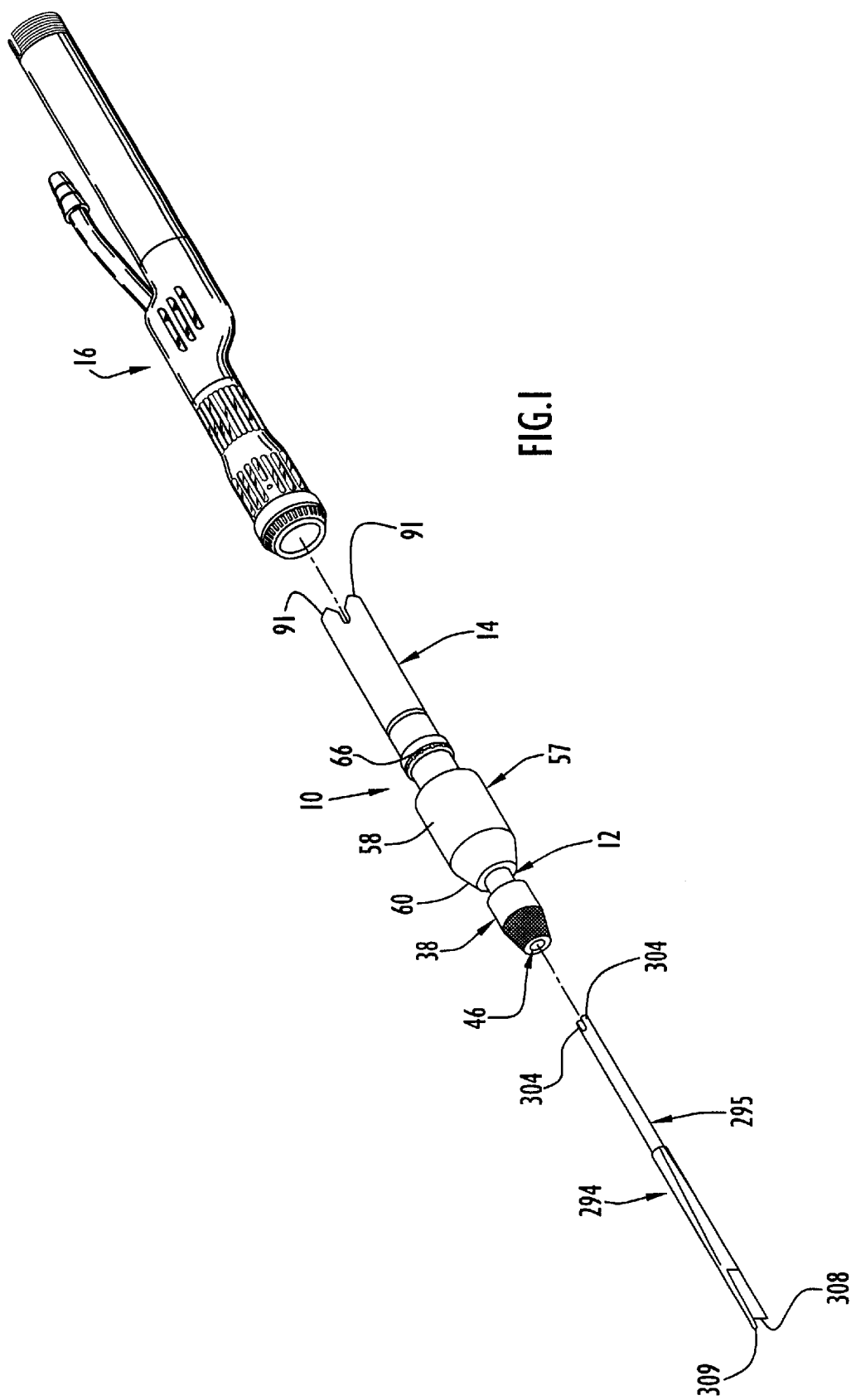
FIG. 1 is an exploded perspective view of a powered surgical handpiece assembly according to the present invention illustrating assembly of a surgical handpiece adapter to a powered surgical handpiece and to a blade or cutting member to be driven by the handpiece via the adapter.

A powered surgical handpiece assembly according to the present invention is illustrated in FIG. 1 and includes a powered surgical handpiece, a surgical handpiece adapter removably coupled to the handpiece and a blade or cutting member removably coupled to the adapter for being driven by the handpiece via the adapter. A surgical handpiece adapter or converter 10 of the powered surgical handpiece assembly is illustrated in FIGS. 1 and 2. The surgical handpiece adapter 10 according to the present invention includes a front drive shaft 12, a rear drive shaft 14 for being rotatably driven by the powered surgical handpiece 16 and a motion converting mechanism 18 for converting or transforming rotary motion of the rear drive shaft 14 into reciprocating motion of the front drive shaft 12. The front drive shaft 12, which is preferably made of 17-4 PH stainless steel having a hardness of H900, includes a distal or forward section 20, a distal or forward intermediate section 22, a proximal or rearward intermediate section 24 and a proximal or rearward section 26. The distal section 20 is formed or provided as a collet 20 including a cylindrical proximal or rearward portion 28 extending distally from the distal intermediate section 22, a truncated conical proximal or rearward intermediate portion 29 extending distally from the proximal portion 28, a cylindrical distal or forward intermediate portion 30 extending distally from the proximal intermediate section 29 and a truncated conical distal or forward portion 31 extending distally from the distal intermediate portion 30.

The proximal portion 28, the proximal intermediate portion 29, the distal intermediate portion 30 and the distal portion 31 are in longitudinal, coaxial alignment, and a longitudinal passage or bore section 32 extends entirely through the distal section 20. The proximal portion 28 and the distal intermediate portion 30 are of constant or uniform cross-section or external diameter along their lengths, respectively, and the external diameters of the proximal portion 28 and the distal intermediate portion 30 are the same or substantially the same. The proximal intermediate portion 29 is of non-constant or non-uniform cross-section or external diameter along its length and has a minimum external diameter joined to or merging with the distal intermediate portion 30 and a maximum external diameter, greater than the external diameters of the proximal portion 28 and the distal intermediate portion 30, defining a transverse shoulder at which the proximal intermediate portion 29 is joined to the proximal portion 28. The distal portion 31 is also of non-constant or non-uniform cross-section or external diameter along its length and has a minimum external diameter at a transverse surface defining a distal end of the adapter 10 and a maximum external diameter, greater than the external diameters of the proximal portion 28 and the distal intermediate portion 30, defining a transverse shoulder at which the distal portion 31 is joined to the distal intermediate portion 30. The maximum external diameter of the distal portion 31 is smaller or less than the maximum external diameter of the proximal intermediate portion 29.

The longitudinal passage section 32 is of uniform or constant diameter or cross-section along the entire length of the distal section 20.

As shown in FIGS. 2 and 3, a plurality of longitudinally extending gaps 33 are formed in the wall of distal section 20, and the gaps 33 extend the entire length of the distal section 20. In the case of front drive shaft 12, four gaps 33 are provided in the distal section 20 at 90 degree spaced locations about a central longitudinal axis of the distal section 20, which is coaxial with a central longitudinal axis of the front drive shaft 12 and with a central longitudinal axis of the adapter 10. In this manner, four longitudinally extending legs are defined by the wall of distal section 20. Each gap 33 has a width between opposing gap edges 34 of adjacent legs, and the gap width is of a first or maximum size when the collet 20 is open as shown in FIGS. 2 and 3. With the collet 20 open, the maximum widths of the gaps 33 are the same or substantially the same, and the gap widths are uniform or constant along the length of the distal section 20.

The distal intermediate section 22 is coaxial with the distal section 20 and has a cylindrical rearward or proximal portion merging with a truncated conical or tapered distal or forward portion, which is joined to or merges with the proximal portion 28 of distal section 20. An external thread 35 is disposed on the cylindrical portion of the distal intermediate section 22 and extends the entire length of such cylindrical portion. The external thread 35 defines a maximum external diameter for distal intermediate section 22 which is larger or greater than the maximum external diameter of proximal intermediate portion 29 of distal section 20. A longitudinal passage or bore section 36 extends entirely through the distal intermediate section 22 and is continuous with passage section 32 of distal section 20. The passage section 36 has a diameter or cross-section, which is uniform or constant along the entire length of distal intermediate section 22, that is the same as the diameter or cross-section of passage section 32.

An operating member in the form of a nut 38 is disposed on the front drive shaft 12 and is threadedly engaged with the thread 35 of distal intermediate section 22 as shown in FIG. 2. The nut 38 has a cylindrical rearward or proximal section and a truncated conical distal or forward section extending distally from the rearward section thereof. A longitudinal passage extends entirely through nut 38 and includes a cylindrical longitudinal passage section 39 disposed in the cylindrical proximal section of nut 38 and a tapered or truncated conical longitudinal passage section 40 disposed in the truncated conical distal section of nut 38. The nut 38 is internally threaded as shown by a thread 41 disposed within and along the cylindrical longitudinal passage section 39. The thread 41 extends along the entire length of the cylindrical longitudinal passage section 39, except for a relatively small, unthreaded proximal length segment of passage section 39. The thread 41 corresponds to the external thread 35 on the distal intermediate section 22 of the front drive shaft 12 and is designed for threaded engagement therewith as shown in FIG. 2. Engagement of thread 41 with the thread 35 allows the nut 38 to be moved longitudinally, proximally and distally, relative to and along the front drive shaft 12 via rotation of nut 38 relative to the drive shaft 12. All or part of the external surface of nut 38 can be knurled, as shown in FIG. 1, or otherwise finished or configured to facilitate grasping and, therefore, operation thereof.

When the nut 38 is in a distal longitudinal position relative to the front drive shaft 12 as shown in FIG. 2, the collet 20 is open and the passage 46 is open so as to allow a proximal end of a blade or cutting member to be inserted therein. A distalmost end surface of the truncated conical distal section of nut 38 is close to or in engagement or abutment with the transverse shoulder of distal portion 31 of front drive shaft 12. The shoulder of distal portion 31 prevents removal of nut 38 from the drive shaft 12. The truncated conical distal section of nut 38 has an angled interior surface in contact or engagement with a more steeply angled exterior surface of proximal intermediate portion 29 of front drive shaft 12 as shown in FIG. 2, the proximal intermediate portion 29 being disposed within the tapered longitudinal passage section 40 of nut 38. When the nut 38 is moved longitudinally, proximally relative to and along the front drive shaft 12, in response to rotation of nut 38 in a first rotational direction relative to front drive shaft 12, the angled interior surface slides along the exterior surface of proximal intermediate portion 29 and forces or moves the legs of collet 20 radially inwardly in the direction of the central longitudinal axis of front drive shaft 12. In this manner, the gap edges 34 of each gap 33 are moved closer to or into contact with one another to reduce the width of gaps 33 and thereby place the collet in a closed position. In the closed position, the passage 46 is closed so as to prevent passage of a proximal end of a blade or cutting member therethrough.

A proximal end of a blade or cutting member can be disposed within the passage section 32 when the collet is open and will be forcefully engaged by the legs of the collet as the collet is closed. Upon sufficient longitudinal, proximal movement of nut 38 relative to and along the front drive shaft 12, the nut 38 will be in a proximal longitudinal position, relative to the front drive shaft 12, wherein sufficient force is exerted by the legs upon the blade or cutting member to firmly couple or secure the blade or cutting member to the front drive shaft and prevent removal of the blade or cutting member from the front drive shaft during use. Accordingly, the proximal longitudinal position of nut 38 corresponds to the closed position for the collet 20 wherein the blade or cutting member is secured or locked onto the front drive shaft 12. Removal or detachment of the blade or cutting member from the front drive shaft 12 and, therefore, from the adapter 10, is effected by untightening the collet, i.e. by rotating the nut 38 in a second rotational direction, opposite the first rotational direction, relative to front drive shaft 12 to effect longitudinal, distal movement of the nut 38 relative to and along the front drive shaft 12. In this manner, the nut 38 is placed in the distal longitudinal position corresponding to the open position for the collet 20 wherein the legs are permitted to move radially outwardly to allow the proximal end of the blade or cutting member to be withdrawn from the passage of the front drive shaft.

The proximal intermediate section 24 is coaxial with the distal intermediate section 22 and is of cylindrical configuration having an external diameter that is the same or substantially the same as the maximum external diameter of distal intermediate section 22. A longitudinal passage or bore section 44 extends part way into the proximal intermediate section 24, the passage section 44 being continuous with the passage section 36 and having the same diameter as passage section 36. The passage section 44 terminates in the proximal intermediate section 24 at a tapered end surface as shown in FIG. 2. The longitudinal passage sections 32, 36 and 44 together define a continuous, unitary, longitudinal passage or bore 46 in the front drive shaft 12, the passage 46 being coaxially aligned with the central longitudinal axis of the front drive shaft. The passage 46 extends longitudinally in the front drive shaft 12 from an open distal end of distal portion 31, which defines the distal end of the adapter, to the end surface within the proximal intermediate section 24.

As shown in dotted lines in FIG. 2, an alignment member 48 is disposed in the passage 46 distally of the end surface thereof. The alignment member 48 includes a post, pin or peg extending in a transverse direction in passage section 44, the alignment member 48 being disposed perpendicular to the central longitudinal axis of the front drive shaft 12. The alignment member 48 may comprise a single, unitary post, pin or peg extending diametrically within the passage section 44 and having opposing ends secured to the wall of front drive shaft 12 forming proximal intermediate section 24. As another example, the alignment member 48 may comprise a pair of individual post, pin or peg segments having first ends, respectively, secured to the wall of front drive shaft 12 forming the proximal intermediate section 24 and second ends terminating within the passage section 44 adjacent or in abutment with one another with the individual post, pin or peg segments being aligned with one another in the transverse diametric direction. The alignment member 48 facilitates proper alignment or positioning of the proximal end of a blade or cutting member within the passage 46 for securement of the blade or cutting member to the adapter 10 in a specific orientation as explained further below.

A plurality of longitudinally extending, partial spherical grooves 50 are formed on an exterior surface of the proximal intermediate section 24 as shown in FIGS. 2 and 4. The grooves 50 have distal ends disposed proximally of the alignment member 48 and proximal ends disposed distally of proximal section 26. The grooves 50 are parallel to the central longitudinal axis of the front drive shaft 12 and are disposed at spaced, radial locations about the central longitudinal axis of the front drive shaft 12 as shown in FIG. 4. In the case of front drive shaft 12, six grooves 50 are provided on the proximal intermediate section 24 at 60 degree spaced, radial locations about the central longitudinal axis of the front drive shaft 12. Each groove 50 is defined by a concave external surface of proximal intermediate section 24 as shown in FIG. 4.

The proximal section 26 of front drive shaft 12 is coaxial with the proximal intermediate section 24 and has an external cylindrical configuration with a uniform or constant external diameter that is greater or larger than the external diameter of proximal intermediate section 24. A cylindrical recess 54 is formed in the proximal section 26 concentric therewith. The recess 54 has a length between an open proximal end of proximal section 26, which defines a proximal end of front drive shaft 12, and a planar end surface 55 within proximal section 26. The recess 54 is of uniform or constant diameter, and a cylindrical aperture or hole 56 is formed in proximal section 26 in communication with the recess 54 as shown in FIG. 2. In particular, the aperture 56 is formed in the wall of front drive shaft 12 forming proximal section 26 and is located near the open proximal end thereof. The aperture 56 is internally threaded and extends entirely through the wall of front drive shaft 12 in a direction transverse or perpendicular to the central longitudinal axis of front drive shaft 12 and therefore, the central longitudinal axis of adapter 10.

The proximal end of front drive shaft 12 is disposed within a housing 57 of adapter 10, the housing 57 including a proximal housing member or body 58 and a distal housing member or nose 60 connected to body 58. The body 58, which is preferably made of 17-4 PH stainless steel having a hardness of H900, includes a cylindrical distal section 62 and a proximal section 63 extending longitudinally, proximally from the cylindrical distal section 62. The cylindrical distal section 62 has a uniform or constant external diameter larger or greater than a uniform or constant external diameter of a cylindrical distal segment of proximal section 63 such that the cylindrical distal section 62 is joined to the cylindrical distal segment of proximal section 63 by a transverse shoulder of body 58. A cylindrical recess 64 is concentrically disposed in the cylindrical distal section 62 and has a length extending proximally from an open distal end of cylindrical distal section 62 to an interior surface of the transverse shoulder of body 58. The length of recess 64 is greater than the length of proximal section 26, thusly providing room in housing 57 for the front drive shaft 12 to reciprocate or move longitudinally, proximally and distally relative thereto. The recess 64 has a uniform or constant diameter of a size to closely receive the external diameter of proximal section 26 while allowing the proximal section 26 and, therefore, the front drive shaft 12, to reciprocate or move longitudinally, proximally and distally, within the recess 64. The proximal section 63 is coaxially aligned with the cylindrical distal section 62 and has a longitudinal passage or bore 65 extending therethrough. The bore 65 is longitudinally or axially aligned with the recess 64 and has a distal end in communication with the recess 64 and a proximal end defining an open proximal end of the body 58, which also defines a proximal end of the housing 57. The bore 65 is of uniform or constant diameter, which is smaller or less than the diameter of recess 64.

An annular flange 66 is concentrically disposed externally on the proximal section 63, and a plurality of partial spherical recesses 67 are disposed on an external surface of flange 66. In the case of body 58, the flange 66 is located between the cylindrical distal section 62 and the open proximal end of the body 58 and is slightly closer to the proximal end of body 58 than to the cylindrical distal section 62. A cylindrical proximal segment of proximal section 63 extends proximally of flange 66 and has a uniform or constant external diameter that is slightly greater than the external diameter of the distal segment of proximal section 63 but less than the external diameter of distal section 62. The distal and proximal segments of proximal section 63 are in coaxial alignment, and the flange 66 has an external diameter greater than the external diameter of the proximal segment of proximal section 63 but less than external diameter of distal section 62. Twelve recesses 67 are provided on flange 66 at 30° spaced, radial locations about a central longitudinal axis of body 58, which is coaxial with the central longitudinal axis of drive shaft 12 when the drive shaft 12 is assembled to the housing 57. The flange 66 is designed to permit the adapter 10 to be releasably coupled with a powered surgical handpiece and, in particular, with the XPS™ StraightShot handpiece as explained further below. A plurality of tapered holes 69, only one of which is visible in FIG. 2, are formed through the wall of body 58 forming the cylindrical distal section 62. The holes 69 are disposed adjacent or close to the open distal end of distal section 62 and extend entirely through the wall of body 58 to communicate with recess 64. In the case of body 58, three holes 69 are provided at 120° spaced locations about the central longitudinal axis of body 58 with the holes 69 being inwardly tapering in a radial direction toward the central longitudinal axis of body 58.

The nose 60 is preferably made of 17-4 PH stainless steel having a hardness of H900 and includes a cylindrical intermediate section 72, a truncated conical distal section 73 and a cylindrical proximal section 74. The cylindrical intermediate section 72 has a uniform or constant external diameter that is the same as the external diameter of cylindrical distal section 62, and the cylindrical proximal section 74 has a uniform or constant external diameter smaller or less than the external diameter of cylindrical intermediate section 72 such that a transverse shoulder is formed or defined on nose 60 where the cylindrical proximal section 74 is joined to the cylindrical intermediate section 72. The external diameter of cylindrical proximal section 74 corresponds to the diameter of recess 64 whereby the cylindrical proximal section 74 can be closely received within the recess 64 with the shoulder of nose 60 in abutment with the distal end of body 58 as shown in FIG. 2. The truncated conical distal section 73 extends distally from the cylindrical intermediate section 72 and has a non-uniform or non-constant external diameter with a maximum external diameter joined to or merging with cylindrical intermediate section 72 and a minimum external diameter at a distal end of nose 60. A shallow cylindrical recess is formed in the distal end of nose 60 in communication with a longitudinal cylindrical bore 75 extending through the nose 60.

As shown in FIGS. 2 and 5, a plurality of apertures 76, corresponding in number to the holes 69, are formed in the wall of nose 60 forming cylindrical proximal section 74. The apertures 76 extend entirely through the wall of nose 60 and thusly communicate with the bore 75. In the case of nose 60, three apertures 76 are provided in nose 60 at 120° spaced locations about a central longitudinal axis of nose 60; and, when the proximal section 74 of nose 60 is disposed in recess 64 with the shoulder of nose 60 in abutment with the distal end of body 58, the apertures 76 are in alignment with the holes 69 as shown in FIG. 2. Preferably, each of the apertures 76 is tapped to receive a screw inserted therein via the holes 69 aligned therewith.

The bore 75 has a uniform or constant diameter of a size sufficiently large to accommodate the external diameter of proximal intermediate section 24 of front drive shaft 12. A plurality of partial spherical grooves 77 are formed in an inner surface of nose 60 defining the bore 75 as shown in FIGS. 2, 4 and 5, and the grooves 77 extend along the entire length of bore 75, except for a small distal length segment of bore 75 defining the shallow recess. The number, configuration and location of the grooves 77 correspond to the number, configuration and location of grooves 50. Accordingly, in the case of nose 60, six grooves 77 are provided in nose 60 at 60° spaced locations about the central longitudinal axis of nose 60, and the grooves 77 are defined by concave interior surfaces of nose 60 corresponding to concave surfaces 51. When the front drive shaft 12 is assembled to the body 58 and the nose 60 as shown in FIG. 2, the proximal intermediate section 24 of the front drive shaft 12 extends entirely through the nose 60, the proximal intermediate section 24 extending through the bore 75 and the shallow recess disposed at the open distal end of the nose 60. As shown in FIG. 4, the grooves 77 of nose 60 are in alignment with the grooves 50 of the front drive shaft 12. Accordingly, each groove 50 is aligned in a radial direction, about the central longitudinal axis of drive shaft 12, with a groove 77 to form an aligned pair of grooves. An annular insert or seal 78, preferably made of stainless steel, is disposed in the shallow recess at the open distal end of nose 60 and has an outer diameter corresponding to the diameter of the shallow recess and an inner diameter corresponding to the external diameter of proximal intermediate section 24 while allowing the drive shaft 12 to move longitudinally therethrough.

As further shown in FIG. 4, a linear bearing including a cage 80, not shown in FIG. 2, and a plurality of spherical balls 81 is preferably disposed in bore 75 between the front drive shaft 12 and the nose 60. Preferably, the cage 80 includes a tubular or hollow cylindrical member having a plurality of circular holes therein for receiving or retaining balls 81, the cage 80 having an outer diameter to be received in the diameter of bore 75 and an inner diameter to receive the external diameter of proximal intermediate section 24. The cage 80 is, as an example, secured to the proximal intermediate section 24 of front drive shaft 12, such as being shrink fit thereon, and has a length corresponding to the length of grooves 50. A first set of six holes is provided in cage 80 and a second set of six holes is provided in cage 80 longitudinally spaced from the first set of six holes. The holes of each set are disposed at 60° spaced, radial locations about the central longitudinal axis of drive shaft 12 such that each hole is aligned with an aligned pair of grooves 50 and 77, as shown in FIG. 4, when the front drive shaft 12 is assembled to the housing 57. Each hole of cage 80 has a diameter corresponding to the diameter of the balls 81, and each ball 81 is disposed in a hole of cage 80 to protrude into the grooves 50 and 77 aligned therewith, each ball 81 being captured between the concave surfaces of the aligned grooves, respectively. Each ball 81 is thusly partly disposed in the groove 50 and partly disposed in the groove 77 of an aligned pair of grooves. The balls 81 are capable of freely rotating within the holes of cage 80, respectively, and the aligned grooves 50 and 77 of the nose 60 and the front drive shaft 12. In addition, as the drive shaft 12 is reciprocated relative to and within the housing 57, each ball 81 moves longitudinally within at least one of the grooves of the associated aligned pair of grooves, or at least one of the grooves of each aligned pair of grooves moves longitudinally relative to the associated ball 81. Where the cage 80 is attached or secured to the front drive shaft 12, for instance, the cage 80 will move with the front drive shaft, and the balls 81 will move longitudinally within the grooves 77 of nose 60. The cage 80 prevents displacement of the balls 81 and thusly maintains the longitudinal spacing and position thereof. It should be appreciated that the cage 80 does not have to be secured to the front drive shaft 12 and that the cage 80 can be secured to the nose 60, in which case the grooves 50 move longitudinally relatively to the balls 81, or can merely be interposed between the nose 60 and the front drive shaft 12 without any mechanical connection between the cage and the front drive shaft or the nose.

The motion converting mechanism 18 includes a cam 82, which is solid and preferably made of 17-4 PH stainless steel having a hardness of H900, coupled with the rear drive shaft 14 and a cam follower 83, which is also preferably made of 17-4 PH stainless steel having a hardness of H900, coupled with the front drive shaft 12. The cam 82 includes a cam head 84 disposed in the recess 54 of proximal section 26 of front drive shaft 12 and a cam shaft or rod 85 extending proximally from cam head 84 and disposed within the bore 65 of proximal section 63 of body 58. The cam shaft 85 extends through the open proximal end of body 58 and is connected to or formed as part of the rear drive shaft 14, which extends externally of the body 58. An annular insert or seal is disposed in the open proximal end of body 58 with the cam shaft 85 extending proximally through the insert or seal. As shown in FIGS. 2 and 6, the cam head 84 includes forward and rearward cam head sections 86 and 86', respectively, between which is defined a groove or track 87. The forward and rearward cam head sections 86 and 86' each have a planar end surface, perpendicular to a central longitudinal axis of cam 82, and a non-planar cam surface, non-perpendicular or disposed at an angle to the central longitudinal axis of cam 82. The planar end surface of forward cam head section 86 defines a distal end of cam head 84 while the planar end surface of rearward cam head section 86' is disposed at a proximal end of cam head 84 such that the track 87 is defined between the cam surfaces.

The forward and rearward cam head sections 86 and 86' each have a maximum length tapering to a minimum length between their planar end surfaces and their non-planar cam surfaces, respectively, the minimum length being located 180° from the maximum length about the central longitudinal axis of cam 82. The forward and rearward cam head sections 86 and 86' are arranged such that the maximum length of forward cam head section 86 is longitudinally aligned with the minimum length of the rearward cam head section 86', and the minimum length of the forward cam head section 86 is longitudinally aligned with the maximum length of the rearward cam head section 86'. Accordingly, the maximum length of the forward cam head section 86 and the minimum length of the rearward cam head section 86' are disposed at the same radial location about the central longitudinal axis of cam 82, while the minimum length of the forward cam head section 86 and maximum length of the rearward cam head section 86' are disposed at a radial location located 180° from the radial location of the maximum length of the forward cam head section 86 and the minimum length of the rearward cam head section 86'. The forward and rearward cam head sections 86 and 86', respectively, each have a maximum external transverse or diametric dimension, which defines a maximum, external transverse or diametric dimension for the cam head 84. An intermediate cam head section of the cam head 84, around which the path of track 87 is defined, extends between the forward and rearward cam head sections and has a cylindrical configuration with an external diameter that is less than or smaller than the maximum external transverse or diametric dimension of the forward and rearward cam head sections. The cam head 84 has a length, between the planar end surfaces thereof, less than the length of recess 54 of proximal section 26 of front drive shaft 12 as shown in FIG. 2. The maximum, external transverse or diametric dimension of cam head 84 corresponds or is close in size to the diameter of recess 54 while allowing the cam head 84 to rotate, relative to the front drive shaft 12, within recess 54 and allowing the front drive shaft 12 to reciprocate or move longitudinally, relative to the cam 82, within the recess 64 of body 58. The cam shaft 85 is rotatable in the bore 65 of proximal section 63 of body 58, and the cam head 84 is rotated with the cam shaft 85 such that the cam 82 rotates relative to the housing 57. The cam 82 is secured in the housing 57 against longitudinal movement relative to the housing 57.

The cam follower 83 includes an externally threaded end secured in aperture 56 of proximal section 26 via engagement of an external thread of the cam follower 83 with the internal thread of aperture 56. The cam follower 83 includes a projection or protrusion 88 longitudinally aligned with the externally threaded end thereof and extending from the externally threaded end thereof into the recess 54 of the proximal section 26. The projection 88 is disposed in the track 87 of cam 82, which is coaxially aligned with the front drive shaft 12. In this manner, the proximal end of the front drive shaft 12 is mechanically coupled to or in driving engagement with the rear drive shaft 14 via the motion converting mechanism. The projection 88 has a length, in a direction parallel to the central longitudinal axis of adapter 10, to be received between the cam surfaces of the cam head 84 and has a height to be received in the space defined by track 87 between the maximum external transverse or diametric dimension of the forward and rearward cam head sections and the external diameter of the intermediate cam head section. When the maximum length of forward cam head section 86 and the minimum length of rearward cam head section 86' are longitudinally aligned with the projection 88 as shown in FIG. 2, the front drive shaft 12 is in a proximalmost longitudinal position, with the distal end of the front drive shaft 12 disposed a minimum longitudinal distance beyond the housing 57. When the cam 82 is rotated from the position shown in FIG. 2, the projection 88 follows the path of track 87 causing the front drive shaft 12 to be moved longitudinally, distally relative to the cam 82 and, therefore, relative to the rear drive shaft 14 and the housing 57. Once the cam 82 has been rotated 180° from the position shown in FIG. 2, such that the minimum length of the forward cam head section 86 and the maximum length of the rearward cam head section 86' are longitudinally aligned with the projection 88, the front drive shaft 12 will be in a distalmost longitudinal position with the distal end thereof disposed a maximum longitudinal distance beyond housing 57. Further rotation of the cam 82 in the same rotational direction causes the front drive shaft 12 to move longitudinally, proximally from the distal most longitudinal position; and, when the cam 82 has been rotated an additional 180°, the front drive shaft 12 will have been returned to the proximalmost longitudinal position. When the rear drive shaft 14 is continuously turned or rotated by the motor of handpiece 16, the front drive shaft 12 is continuously reciprocated or moved longitudinally back and forth, distally and proximally. As the front drive shaft 12 is reciprocated, the proximal section 26 thereof moves longitudinally within the recess 64 of body 58.

The rear drive shaft 14 for adapter 10 is preferably made of 17-4 PH stainless steel having a hardness of H900 and has a distal end secured to a proximal end of cam shaft 85, the rear drive shaft 14 being in axial alignment with cam 82. The rear drive shaft 14 has a proximal end for being removably coupled with the handpiece 16. The rear drive shaft 14 can be formed as a separate member secured to cam shaft 85 or the rear drive shaft can be formed integrally, unitarily with the cam shaft; and, accordingly, the rear drive shaft 14 cannot move longitudinally relative to the housing 57. The rear drive shaft 14 is at least partly tubular with the proximal end thereof being open and in communication with a lumen extending distally in the rear drive shaft from the open proximal end thereof. A plurality of oblong slots 90 are formed in the proximal end of rear drive shaft 14 at 90° spaced locations about a central longitudinal axis of rear drive shaft 14, which is coaxial or coincident with the central longitudinal axis of adapter 10. The slots 90 extend longitudinally, parallel to the central longitudinal axis of adapter 10, to define a plurality of spaced prongs 91. Each slot 90 has a distal portion of uniform width and a proximal portion of increasing width in the proximal direction such that the proximal portions of the slots 90, respectively, flare out from the distal portions thereof to provide prongs 91 with triangular shaped tips. The rear drive shaft 14 is thusly adapted to be operatively coupled with the handpiece 16, which is the XPS™ StraightShot handpiece of Xomed, Inc. disclosed in the patent applications incorporated herein by reference. In particular, drive pins of the front drive shaft of the handpiece 16 are disposed in a pair of opposed slots 90 in driving engagement with prongs 91 in the same manner as disclosed in the prior applications incorporated herein by reference for coupling a blade or cutting member to the handpiece. In this manner, the proximal end of the rear drive shaft has a configuration to mate with the drive shaft of the handpiece.

The adapter 10 is coupled with the handpiece 16 by moving the middle collet member of the handpiece longitudinally proximally, relative to the outer collet member of the handpiece, to the retracted position, causing ball bearings within the middle collet member to be aligned with the forward passage segment of the middle collet member. The proximal end of rear drive shaft 14 is introduced in the longitudinal passage of the middle collet member and is moved longitudinally, proximally further into the handpiece to enter the longitudinal passage of the inner collet member of the handpiece 16 such that the drive pins of the front drive shaft of the handpiece enter the slots 90, the triangular prongs 91 providing a self-centering function facilitating entry of the drive pins of the handpiece 16 into a pair of opposed slots 90 of the rear drive shaft 14 of the adapter 10. The annular flange 66 on body 58 enters the passage of the inner collet member, causing the ball bearings of the middle collet member to be moved outwardly from their holes. When the rear drive shaft 14 is inserted in the handpiece 16 in proper engagement with the front drive shaft of the handpiece, a proximal surface or face of flange 66 will be in abutment with an internal shoulder of the inner collet member of the handpiece 16, and the partial spherical recesses 67 of flange 66 will be in alignment with the holes that receive the ball bearings of the handpiece. When the middle collet member of handpiece 16 is thereafter released, it is returned to the extended position due to the bias of a spring, causing the ball bearings to be moved inwardly into the partial spherical recesses 67 of flange 66. Accordingly, flange 66 of adapter 10 is prevented by the ball bearings from moving longitudinally and rotationally relative to the handpiece 16, and the adapter 10 is therefore locked in place on the handpiece 16 as described in the prior applications incorporated herein by reference. With the adapter 10 thusly coupled with the handpiece 16, rotation of the drive shaft of the handpiece 16 is effected by an electric motor of the handpiece 16, causing rotation of the rear drive shaft 14 therewith. Rotation of rear drive shaft 14 by handpiece 16 causes the front drive shaft 12 of the adapter 10 to be reciprocated via conversion or transformation of the rotary motion of the rear drive shaft 14 into reciprocating motion of the front drive shaft 12 via the motion converting mechanism 18. Operation of handpiece 16 to rotate the drive shaft thereof is typically controlled via a console or a foot switch as described in the prior applications incorporated herein by reference.

The adapter 10 is preferably made of durable, medically acceptable materials, such as stainless steel or hard coated anodized aluminum or titanium, for example, capable of being sterilized to medical standards, such as by steam or flash autoclaving, gas sterilization and/or soaking in a disinfectant solution. Accordingly, the adapter 10 is designed for repeated use. As described in the prior applications incorporated herein by reference, the handpiece 16 is also designed for repeated use. The adapter 10 can include various sizes of front and rear drive shafts and/or motion converting mechanisms in accordance with the types of blades or cutting members to be driven by the adapter, the stroke desired for the blades or cutting members and/or the force or stress to which the blades or cutting members are to be subjected during use. The difference between the maximum and minimum lengths of the rearward cam head section 86' defines the stroke for the front drive shaft 12, i.e. the distance that the distal end of the front drive shaft 12 travels between the proximalmost and the distalmost longitudinal positions. Accordingly, it should be appreciated that the stroke of the front drive shaft 12 and, therefore, the stroke of the blade or cutting member coupled therewith, can be varied or adjusted with the use of different cam heads. In a preferred adapter according to the present invention for use with a reciprocating rasp as described below, the cam head is designed to provide a stroke of 3.0 mm. In another preferred adapter according to the present invention for use with a reciprocating osteotome as described below, the cam head is designed to provide a stroke of 2.0 mm.

An alternative cam is illustrated at 182 in FIG. 7. The cam 182 is similar to cam 82 except that the cam head 184 for cam 182 is configured so as to obtain a smaller stroke for the front drive shaft 12 and, therefore, for a blade or cutting member coupled to the front drive shaft 12. Cam head 184 includes track 187 between forward and rearward cam head sections 186 and 186', respectively. The rearward cam head section 186' has a maximum length that is less than the maximum length of rearward cam head section 86' and has a minimum length that is greater than the minimum length of rearward cam head section 86'. Accordingly, the difference between the maximum and minimum lengths of rearward cam head section 186' is less than the difference between the maximum and minimum lengths of rearward cam head section 86' such that the stroke provided by cam head 184 is smaller than that provided by cam head 84.

In the powered surgical handpiece assembly of FIG. 1, the adapter 10 is coupled with the XPS™ StraightShot handpiece 16 and with an osteotome 294 described below. It should be appreciated, however, that the adapter 10 can be coupled with various handpieces and cutting members to form a powered surgical handpiece assembly. The adapter 10 coupled with the osteotome 294 forms a handpiece adapter assembly. However, a handpiece adapter assembly can be formed by adapter 10 coupled with various cutting members.

A blade or cutting member 94 according to the present invention for being reciprocatively driven by a reciprocative driver is illustrated in FIGS. 8 and 9 and is a surgical rasp, preferably made of stainless steel, including an elongate, cylindrical member or shaft 95, a tissue cutting element 96 disposed at a distal end of shaft 95 and a suction passage 97 communicating with the cutting element 96. The cutting element 96 has a wedge shaped configuration with a planar lower surface 98 and a gently curved or rounded upper surface 99 disposed at an angle to lower surface 98. The lower surface 98 has an oblong perimetrical configuration defined generally as a rectangle with curved or rounded corners. The upper surface 99 is joined to or merges with the perimeter of lower surface 98. The cutting element 96 has a distal end defined by a curved or arcuate edge portion of its perimeter and has a height, between lower and upper surfaces 98 and 99, respectively, that increases in the proximal direction from the distal end thereof. A proximal end of the cutting element 96 is joined or connected to the distal end of shaft 95 with the lower surface 98 parallel to but laterally offset from a central longitudinal axis of shaft 95. The lower surface 98 is also laterally offset from an external diametric or circumferential surface of shaft 95 such that the lower surface 98 protrudes laterally beyond the shaft 95.

An oval shaped hole or aperture 92 is formed in lower surface 98 in communication with a channel 93 that extends angularly, proximally from the hole 92 through the cutting element 96, the hole 92 having a center that is disposed in a plane containing the central longitudinal axis of shaft 95. Preferably, the channel 93 is disposed at an angle of 30° to the lower surface 98. A plurality of tissue cutting, removing or abrading ridges 100 are disposed on the entire remaining area of lower surface 98 and are adapted to cut, remove, shape or abrade anatomical tissue, such as bone, when the cutting element 96 is reciprocated along the tissue. The ridges 100 can have various configurations, such as being formed by triangular or diamond-shaped protuberances as shown, and can be arranged in various patterns on lower surface 98. The ridges 100 can be of various sizes or sharpness such that a series of rasps can be provided having various degrees of coarseness or sharpness, such as fine, medium and coarse degrees of coarseness or sharpness. The suction passage 97 includes a suction tube 89, preferably made of stainless steel, secured within the channel 93 and having an open distal end 101 terminating at the lower surface 98 and an open proximal end terminating at a fitting 102 disposed proximally of cutting element 96. The open distal end 101 of the suction passage 97 defines an inlet opening along the lower surface 98 through which anatomical debris, such as blood and/or anatomical tissue, enters the lumen of the suction tube 89 to be transported away from the cutting element 96 and, therefore, away from an operative site at which the blade or cutting member 94 is used. The fitting 102 defines an outlet opening of the suction passage 97 disposed proximally of the distal end of shaft 95.

It should be appreciated that the open distal end 101 of the suction tube 89 can be disposed within the channel 93 without being aligned or flush with or disposed in the same plane as lower surface 98, in which case the suction passage 97 will be formed by the suction tube 89 and by a portion of the channel 93 with the hole 92 in lower surface 98 constituting the inlet opening of the suction passage. The fitting 102 is adapted to be connected to a first end of a length of flexible, plastic tubing having a second end coupled or connected with a source of suction, such as a suction pump or vacuum. The suction tube 89 extends angularly and rearwardly from the upper surface 99 of the cutting element 96 and extends proximally alongside the shaft 95. A proximal length segment of the suction tube 89 is angled upwardly from the shaft 95 and terminates at the fitting 102. Preferably, the suction tube 89 is secured to the shaft 95, such as by welding, soldering or various adhesives. A central longitudinal axis of the suction passage 97 is disposed in the same plane as the central longitudinal axis of shaft 95. The shaft 95, which preferably is solid, has a diameter for being closely received within the passage 46 of front drive shaft 12. A transverse slot 103 is formed through the proximal end of shaft 95 and defines a pair of spaced prongs 104 for being disposed on opposite sides, respectively, of the alignment member 48 of the adapter 10. In this manner, the proximal end of the cutting member is configured to engage the alignment member of the adapter when the cutting element is in a specific orientation relative to the adapter. The specific orientation for the cutting element relative to the adapter corresponds to the configuration of the proximal end of the rear drive shaft of the adapter in that the rear drive shaft of the adapter is configured to drivingly engage the drive shaft of the handpiece when the cutting element is in the specific orientation relative to the handpiece. The specific orientation for the cutting element is the desired orientation for use of the cutting member via manual manipulation of the handpiece when grasped and held in the normal or intended manner for grasping and holding of the handpiece.

The cutting members used in the powered surgical handpiece assembly according to the present invention can have cutting elements designed in various ways with various configurations in accordance with the types of cutting functions to be performed therewith. For example, the cutting element can be designed to cut anatomical tissue, such as bone, by abrading the anatomical tissue as in the case of cutting element 96, by incising, resecting or otherwise removing, shaping and/or contouring the tissue. Accordingly, as used herein, "cutting" is intended to include abrasion, incision, removal, shaping and/or contouring of anatomical tissue as well as other tissue cutting functions involving reciprocation of the cutting element.

The blade or cutting member 94 is coupled with the adapter 10 by inserting the proximal end of shaft 95 into the longitudinal passage section 32 of distal section 20 of front drive shaft 12 with the nut 38 in the distal longitudinal position so that the collet is open. The proximal end of shaft 95 is moved through longitudinal passage section 32 into and through the longitudinal passage section 36 of distal intermediate section 22 and into the longitudinal passage section 44 of proximal intermediate section 24. The shaft 95 is rotated, as necessary, while being pushed proximally until the alignment member 48 enters the slot 103. The prongs 104 will then be disposed on opposite sides of the alignment member 48, which prevents rotation of the shaft 95 relative to the front drive shaft 12. Engagement of the prongs 104 with the alignment member 48 can be confirmed tactilely, by being felt by the surgeon, and audibly, by a clicking sound, as the alignment member engages the prongs. The central longitudinal axis of shaft 95 will be coaxial with the central longitudinal axis of the adapter 10.

Figure 14:
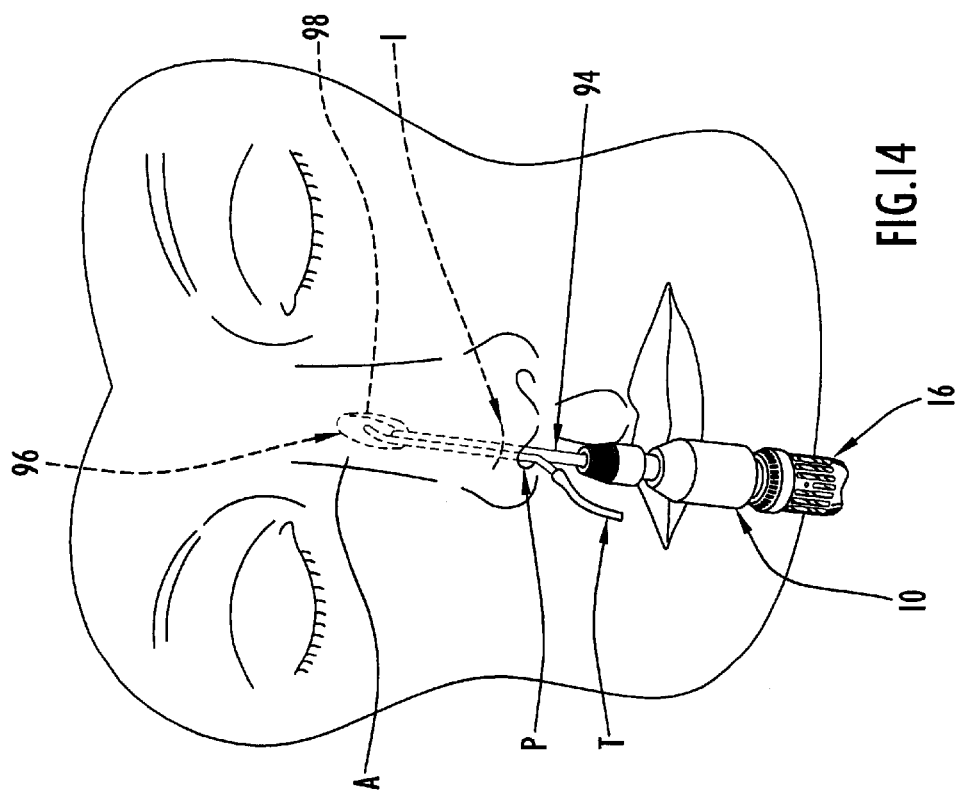
FIG. 14 is a perspective view illustrating use of the rasp of FIG. 8 to reshape the nasal bone of a patient in a facial procedure.

When the front drive shaft 12 is in the rotational position illustrated in FIG. 2, the alignment member 48 is oriented vertically; and, when the vertically oriented alignment member is disposed in the slot 103, the blade or cutting member 94 will be positioned such that the lower surface 98 faces downwardly relative to the adapter 10 and relative to the handpiece 16 when the adapter is coupled to the handpiece 16 and the handpiece 16 is in the normal or intended position for being grasped or held by a surgeon. An indicating or reference mark can be provided on the adapter 10 indicative of the position of the alignment member 48. The adapter 10 can be thusly assembled to the handpiece 16 and the blade or cutting member 94 can be assembled to the adapter 10 such that the cutting element is in the specific orientation for use thereof. In the case of cutting member 94, the cutting element 96 is oriented for use as a rasp with the cutting surface 98 facing downwardly and disposed in a plane perpendicular to the plane containing the central longitudinal axis of shaft 95, adapter 10 and the drive shaft of handpiece 16, respectively, as shown in FIG. 14.

A handpiece adapter assembly is formed by rasp 94 coupled with adapter 10. It should be appreciated however, that a handpiece adapter assembly can be formed by rasp 94 coupled to various adapters capable of reciprocating the rasp 94 in response to the adapters being rotatably driven. A powered surgical handpiece assembly is formed by rasp 94 coupled with the XPS™ StraightShot handpiece 16 via the adapter 10. However, a powered surgical handpiece assembly can be formed by rasp 94 coupled with various rotary handpieces via various adapters capable of reciprocating the rasp 94 in response to the adapters being rotatably driven by the handpieces.

Figure 17:
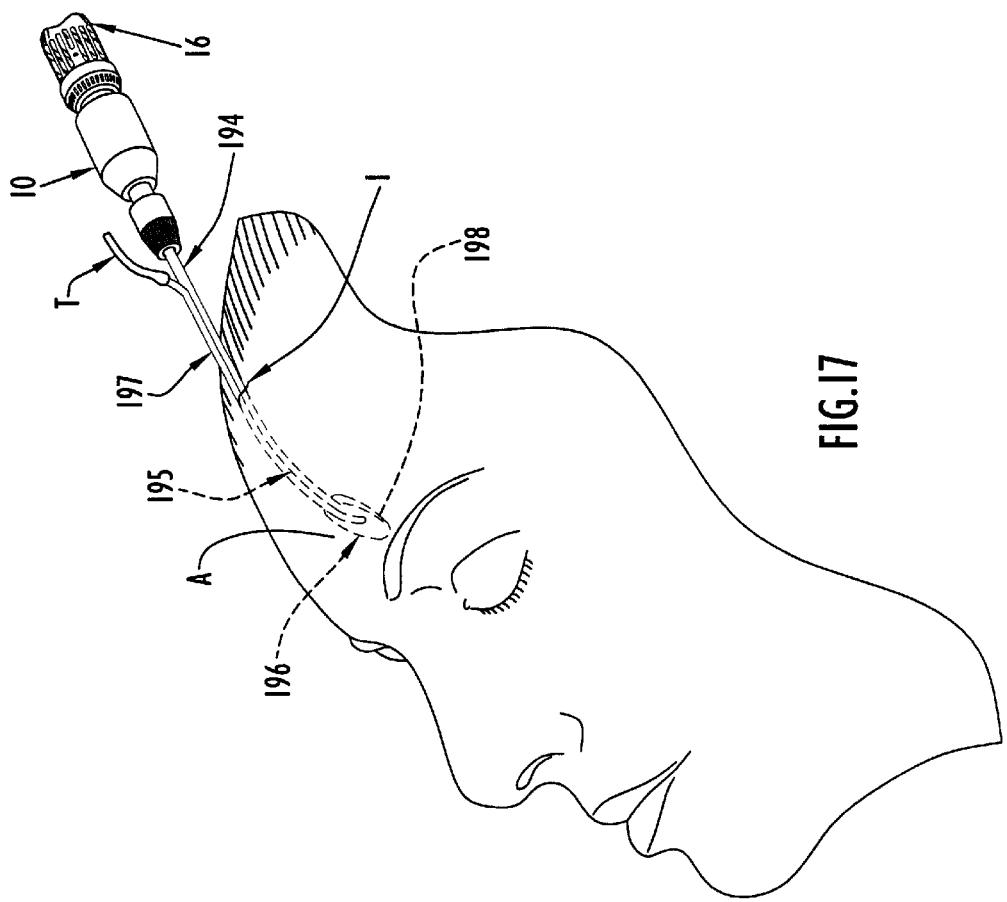
FIG. 17 is a perspective view illustrating use of the rasp of FIG. 10 in a supraorbital procedure.

An alternative blade or cutting member according to the present invention, which is also a rasp, is illustrated at 194 in FIG. 10. The cutting member 194 is similar to the cutting member 94 except that the shaft 195 of cutting member 194 has a longitudinally straight proximal length segment and a longitudinally curving distal length segment. The cutting element 196 of cutting member 194 is similar to cutting element 96 and has a proximal end joined to a distal end of shaft 195. The suction passage 197 for cutting member 194 is similar to the suction passage 97, except that the suction tube 189 of suction passage 197 follows the curvature of the distal length segment of shaft 195 and extends further proximally of the distal end of shaft 195 than the suction tube 89. The cutting member 194 is particularly advantageous for use in supraorbital facial procedures, and the curvature of shaft 195 corresponds to or mimics the natural curvature of the human head and, in particular, the forehead, between the upper hairline and the eyebrow. As with cutting member 94, the cutting member 194 has prongs (not visible in FIG. 10) to insure proper alignment of the cutting member 194 relative to the adapter 10 and the handpiece 16. When the prongs of cutting member 194 are disposed on opposite sides of the alignment member 48, the proximal length segment of shaft 195 will be coaxial with the central longitudinal axis of front drive shaft 12. The cutting surface 198 of cutting element 196 will face downwardly relative to the adapter 10, and relative to the handpiece 16 when the adapter 10 is coupled thereto, and the cutting surface 198 will be disposed at an acute angle to the central longitudinal axis of adapter 10 as shown in FIG. 17.

As with the rasp 94, the rasp 194 forms a handpiece adapter assembly when the rasp 194 is coupled to adapter 10. However, a handpiece adapter assembly can be formed by rasp 194 coupled with various adapters capable of reciprocating the rasp 194 in response to the adapters being rotatably driven. A powered surgical handpiece assembly is formed by rasp 194 coupled with the XPS™ StraightShot handpiece 16 via the adapter 10. It should be appreciated, however, that a powered surgical handpiece assembly can be formed by rasp 194 coupled with various rotary handpieces via various adapters capable of reciprocating the rasp 194 in response to the adapters being rotatably driven by the handpieces.

A blade or cutting member, which is an osteotome, to be reciprocatively driven by the handpiece 16 via the adapter 10 is illustrated at 294 in FIGS. 1, 11 and 12. The cutting member 294 includes an elongate cylindrical member or shaft 295, the proximal end of which is provided with a slot 303 forming prongs 304, and the distal end of which is joined to or formed as a cutting element 296. The cutting element 296 has a longitudinally straight proximal length portion joined to the distal end of shaft 295 and including flat or planar lateral surfaces 305a and 305b connected by curved upper and lower surfaces 306a and 306b, respectively. The lateral surfaces 305a and 305b are angled inwardly toward one another from the distal end of shaft 295 such that the proximal length portion of cutting element 296 is of gradually decreasing width, defined between lateral surfaces 305a and 305b, in the distal direction. The cutting element 296 has a longitudinally straight distal length portion merging and continuous with the proximal length portion thereof. The distal length portion of cutting element 296 has a curved upper surface 306a' and a substantially flat lower surface 306b' merging and continuous with the upper and lower surfaces 306a and 306b, respectively. An upper part of the distal length portion of cutting element 296 extends further distally than a lower part thereof and has flat or planar lateral surfaces 305a' and 305b', respectively, merging and continuous with lateral surfaces 305a and 305b, respectively.

The lower part of the distal length portion of cutting element 296 has lateral surfaces 305a" and 305b" merging and continuous with the lateral surfaces 305a and 305b, respectively. The lateral surfaces 305a' and 305b' are angled inwardly toward one another from the lateral surfaces 305a and 305b, respectively, such that the upper part of the distal length portion is of gradually decreasing width, defined between the lateral surfaces 305a' and 305b', in the distal direction. In the case of the osteotome 294, the lateral surfaces 305a' and 305b' are angled inwardly toward one another at a greater or steeper angle than surfaces 305a and 305b. It should be appreciated, however, that the lateral surfaces 305a' and 305b' can follow or continue the angle or taper of the lateral surfaces 305a and 305b, respectively. The lateral surfaces 305a" and 305b" are also angled inwardly toward one another from the lateral surfaces 305a and 305b, respectively, the lateral surfaces 305a" and 305b" being angled inwardly toward one another at a greater or steeper angle than surfaces 305a' and 305b'. The lower part of the distal length portion is therefore of gradually decreasing width, defined between lateral surfaces 305a" and 305b", in the distal direction, and the width of the lower part decreases a greater amount or rate in the distal direction than the width of the upper part. Accordingly, the lateral surfaces 305a" and 305b" are recessed with respect to the lateral surfaces 305a' and 305b', respectively, such that the lateral surfaces 305a" and 305b" are disposed laterally inwardly of the lateral surfaces 305a' and 305b', respectively, with the lateral surfaces 305a' and 305b' disposed laterally outwardly of the lateral surfaces 305a" and 305b", respectively.

The lateral surface 305a' is connected to the lateral surface 305a" by a transverse surface 307a, and the lateral surface 305b' is connected to the lateral surface 305b" by a transverse surface 307b. The lateral surfaces 305a" and 305b", merge or connect distally with one another at a transverse distal edge 308, which is transverse to the transverse surfaces 307a and 307b. The edge 308 is in line with but is transverse to the central longitudinal axis of shaft 295, which defines the central longitudinal axis of the cutting member 294. The lateral surfaces 305a' and 305b' of the upper part of the distal length portion of the cutting element 296 terminate or merge distally at a rounded or blunt tip 309 disposed distally of edge 308. The distal edge 308 is sharp and forms a cutting edge capable of cutting anatomical tissue, such as bone, when the cutting member 294 is advanced by the surgeon into and/or along the tissue while being reciprocated by the adapter. The blunt tip 309 leads the cutting element 296 as the cutting member 294 is advanced into and/or along the anatomical tissue, the tip 309 and the upper part of the distal length portion serving to guide the cutting element 296 and to separate, protect or guard adjacent or surrounding anatomical tissue from the cutting edge 308. The cutting member 294 is particularly advantageous for use in forming a straight medial cut in the nasal bone of a patient in a rhinoplasty procedure as described further below.

As with the rasps 94 and 194, the osteotome 294 forms a handpiece adapter assembly when the osteotome 294 is coupled to adapter 10. However, a handpiece adapter assembly can be formed by osteotome 294 coupled with various adapters capable of reciprocating the osteotome 294 in response to the adapter being rotatably driven. A powered surgical handpiece assembly is formed by osteotome 294 coupled with the XPS™ StraightShot handpiece 16 via the adapter 10. It should be appreciated, however, that a powered surgical handpiece assembly can be formed by osteotome 294 coupled with various rotary powered surgical handpieces via various adapters capable of reciprocating the osteotome 294 in response to the adapters being rotatably driven by the handpieces.

As noted above, various adapters can be used in the handpiece adapter assemblies and the powered surgical handpiece assemblies including adapters using an off-axis cam as the motion converting mechanism. For example, the rear drive shaft of the adapter may be used to rotate an off-axis roller of the adapter in an orbital manner causing a rocker engaged with the roller to exert a linear force on the front drive shaft via a link coupled to the rocker and the front drive shaft.

Another blade or cutting member, which is also an osteotome, to be reciprocatively driven by the handpiece 16 via the adapter 10 is illustrated at 394 in FIG. 13. The cutting member 394 is similar to the cutting member 294 except that the distal length portion of the cutting element 396 of cutting member 394 is longitudinally curved or bent in a lateral direction. Accordingly, the lateral surfaces 405a', 405b', 405a" and 405b" of cutting element 396 are not flat or planar but, rather, are curved in the lateral direction. In this manner, the cutting edge 408 and the blunt tip 409 are both laterally offset from and not in line with the central longitudinal axis of shaft 395. The cutting member 394 is particularly advantageous for use in forming a curved lateral cut in the nasal bone of a patient in a rhinoplasty procedure as explained further below.

As with the rasps 94 and 194 and the osteotome 294, the osteotome 394 forms a handpiece adapter assembly when the osteotome 394 is coupled to adapter 10. However, a handpiece adapter assembly can be formed by osteotome 394 coupled with various adapters capable of reciprocating the osteotome 394 in response to the adapters being rotatably driven. A powered surgical handpiece assembly is formed by osteotome 394 coupled with the XPS™ Straight-Shot handpiece 16 via the adapter 10. It should be appreciated, however, that a powered surgical handpiece assembly can be formed by osteotome 3934 coupled with various rotary powered surgical handpieces via various adapters capable of reciprocating the osteotome 394 in response to the adapters being rotatably driven by the handpieces.

For use in a surgical procedure, such as a facial procedure, the adapter 10 is coupled with the handpiece 16 and a blade or cutting member selected in accordance with the surgical procedure to be performed is coupled with the adapter 10 as described above. FIG. 14 illustrates the rasp 94 coupled with the adapter 10, which is coupled with the XPS™ Straight-Shot handpiece 16, forming a powered surgical handpiece assembly for use in a rhinoplasty procedure. In addition, a length of tubing Tomita et al is connected to the fitting 102 and to a source of suction (not shown). In the rhinoplasty procedure illustrated in FIG. 14, the cutting element 96 of the rasp 94 is introduced between the nasal bone of the patient and the anatomical tissue A overlying the nasal bone. The cutting element 96 is introduced via an incision I made in the nasal passage P of the patient's nose as shown in FIG. 14 or via an incision or flap made at or near the tip of the patient's nose. The incision I is preferably no larger than necessary to receive the cutting element 96 to minimize trauma to the patient. The cutting element 96 is introduced at an operative site between the nasal bone and the overlying tissue A with the cutting element in the specific orientation so that the cutting surface 98 is disposed over and faces an area of the nasal bone that is to be reshaped or contoured via abrasion by the cutting surface 98. The cutting element 96 is positioned at the proper location over the nasal bone via manipulation of handpiece 16 by the surgeon. The skin of the patient overlying the location on the nasal bone that is to be reshaped or contoured can be marked, such as with a medically acceptable ink, to facilitate proper positioning of the cutting element 96. Proper positioning of the cutting element 96 can be confirmed via palpation of the patient's nose by the surgeon since the cutting element can be felt beneath the overlying anatomical tissue A and can be seen as a bulge in the tissue A.

Once the cutting element 96 is properly located at the location on the nasal bone that is to be shaped or contoured, the handpiece 16 is actuated, typically via an appropriate switch or foot pedal as described in the prior applications incorporated herein by reference, to rotate or turn the motor of the handpiece 16. As the motor of handpiece 16 is turned or rotated, rotary motion of the drive shaft of the handpiece 16 is converted to reciprocating motion of the front drive shaft 12 of adapter 10 via the motion converting mechanism 18. For the rasp 94, the motor will typically be operated at a speed of 5,000 RPM. The rasp 94 is reciprocated with the front drive shaft 12; and, when the cutting surface 98 is placed in contact with the nasal bone, the ridges 100 of the cutting element 96 abrade and remove some of the nasal bone such that the nasal bone is reshaped or contoured. As the cutting element 96 is reciprocated by the handpiece 16, the handpiece assembly is also moved longitudinally and/or laterally by the surgeon with the cutting surface 98 in contact with the nasal bone, allowing the surgeon to reshape or contour the nasal bone in accordance with a desired result.

As the cutting element 96 is reciprocated, suction from the suction source is applied at the operative site via the suction passage 97. In this manner, anatomical debris, including blood and/or tissue, enters or is drawn into the inlet opening of the suction passage and is removed from the operative site via the suction passage and the tubing Tomita et al for withdrawal from the patient's body. Once sufficient bone has been removed with the cutting element 96 so that the nasal bone is shaped or contoured as desired, the rasp 94 is withdrawn from the patient's nose via incision I. Proper shaping or contouring of the nasal bone and removal of a desired amount of bone can be confirmed by the surgeon via palpation of the patient's nose. In addition, it should be appreciated that the procedure can be performed as a minimally invasive procedure wherein a remote viewing device, such as an endoscope, is used to provide visualization of the operative site. As an example, an image receiving end of an endoscope can be introduced at the operative site through the same or a different incision in the patient's nose.

Figure 15:
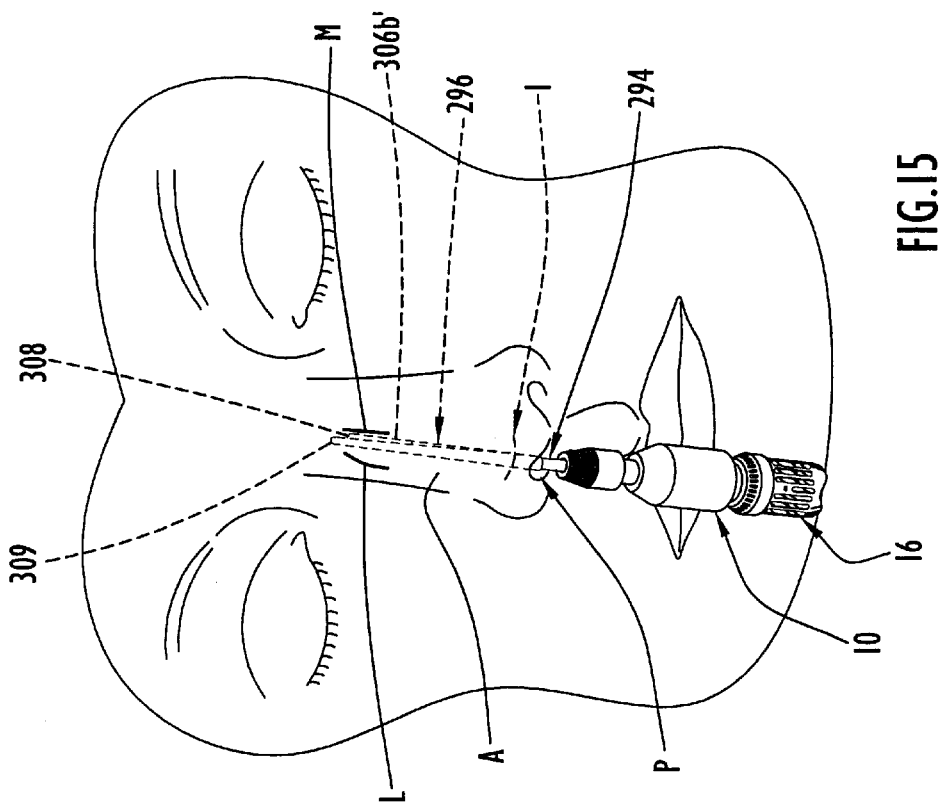
FIG. 15 is a perspective view illustrating use of the osteotome of FIGS. 1, 11 and 12 to make a straight medial cut in the nasal bone of a patient in a rhinoplasty procedure.
Figure 16:
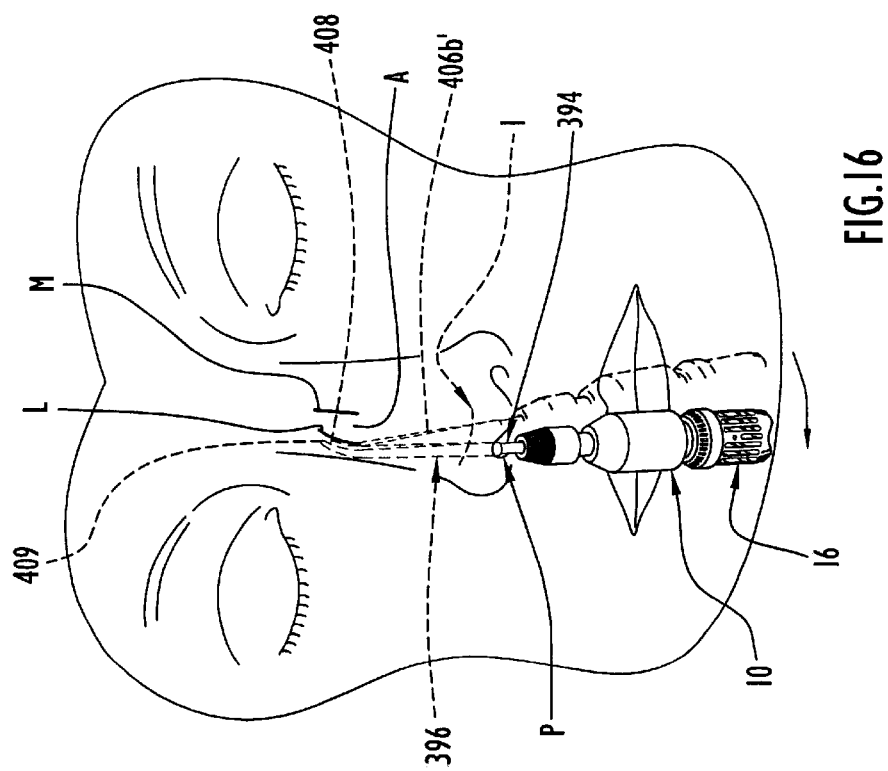
FIG. 16 is a perspective view illustrating use of the osteotome of FIG. 13 to make a curved lateral cut in the nasal bone of a patient in a rhinoplasty procedure.

FIGS. 15 and 16 illustrate use of the osteotomes 294 and 394 in conjunction with adapter 10 and handpiece 16 to make medial and lateral cuts in the nasal bone of a patient in a rhinoplasty procedure. As an initial step in the procedure, the skin of the patient's nose is marked with markings M and L at locations overlying selected sites on the nasal bone at which medial and lateral cuts, respectively, are to be made in the nasal bone, the markings M and L being generally indicative of the configurations or paths and the lengths for the medial and lateral cuts, respectively. FIG. 15 illustrates the osteotome 294 coupled with the adapter 10, which is coupled with handpiece 16, to form a powered surgical handpiece assembly. The cutting element 296 is introduced between the nasal bone of the patient and the anatomical tissue A overlying the nasal bone. The cutting element 296 is introduced through an incision I made in the nasal passage P as shown in FIG. 15 or via an incision or flap made at or near the tip of the patient's nose. The incision I is preferably no larger than necessary to receive the cutting element 296 to minimize trauma to the patient. The cutting element 296 is introduced at an operative site between the nasal bone and the overlying tissue A with the cutting element 296 in the specific orientation so that the lower surface 306b' is disposed upon the nasal bone with the cutting edge 308 at a site corresponding to a lower or beginning end of the medial cut. The blunt tip 309 leads and guides the cutting edge 308 to the site on the nasal bone and separates and protects surrounding anatomical tissue from injury by the cutting edge 308 as the cutting edge 308 is advanced to the site via manipulation of handpiece 16 by the surgeon. Proper positioning of the cutting element 296 can be confirmed via palpation of the patient's nose since the cutting element 296 can be felt beneath the overlying anatomical tissue A and since the cutting element forms a visible bulge in the overlying tissue.

Once the cutting edge 308 is properly disposed at the site on the nasal bone at which the medial cut is to begin, the handpiece 16 is actuated causing reciprocation of cutting member 294 via the adapter 10. For the osteotome 294, the motor of the handpiece will typically be operated at a speed of 6,000 RPM. As the cutting member 294 is reciprocated, the cutting edge 308 is moved into and along the nasal bone via manual manipulation of the handpiece assembly formed by adapter 10, handpiece 16 and cutting member 294. In particular, the handpiece assembly is advanced longitudinally distally or forwardly by the surgeon while the cutting edge 308 is moved into the nasal bone. The handpiece 16 may be angled upwardly relative to the nasal bone, as it is being distally advanced, to facilitate movement of the cutting edge 308 into the bone. As indicated by the marking M, the medial cut has a straight configuration or path, and the cutting element 296 is advanced distally or forwardly along this straight configuration or path to an upper or terminal end for the medial cut. The cutting edge 308 in contact with the nasal bone as the cutting element 296 is moved forwardly therealong while being reciprocated at the same time, causes a straight medial cut of desired length to be formed in the nasal bone. The medial cut is formed very quickly with the reciprocating osteotome or cutting member 294; and, once the medial cut is formed, the cutting member 294 is withdrawn from the patient's nose via the incision I. Proper formation of the medial cut can be confirmed via palpation of the nose and/or a remote viewing device where the procedure is performed as a minimally invasive procedure.

Upon completion of the medial cut and withdrawal of the cutting member 294 from the patient's nose, the osteotome or cutting member 394 is used to form a lateral cut in the nasal bone corresponding to marking L. The cutting member 294 is removed from the adapter 10, which remains coupled with the handpiece 16, and the cutting member or osteotome 394 is coupled with the adapter 10 to form another powered surgical handpiece assembly. The cutting element 396 of osteotome 394 is introduced at the operative site through the incision I in nasal passage P. The cutting element 396 is introduced between the nasal bone and the overlying anatomical tissue A with the cutting element 396 in the specific orientation so that the lower surface 406b' is disposed upon the nasal bone with the cutting edge 408 at a site corresponding to a lower or beginning end of the lateral cut. The blunt tip 409 leads and guides the cutting edge 408 as the cutting edge 408 is advanced to the site on the nasal bone and protects surrounding tissue from injury or damage by the cutting edge 408. Proper positioning of the cutting element 396 can be confirmed by feel and by observing a bulge in the overlying tissue A due to the presence of the cutting element therebeneath. As indicated by the marking L, the lateral cut is spaced laterally from the medial cut and has a curved configuration or path. Accordingly, the osteotome or cutting member 394 that is being used by the surgeon to make the lateral cut has its distal portion curving laterally in the same direction as the lateral cut as illustrated in FIG. 16.

Once the cutting edge 408 has been positioned at the proper site on the nasal bone at which the lateral cut is to begin, the handpiece 16 is actuated causing reciprocation of the cutting member 394 via the adapter 10. For the osteotome 394, the motor of the handpiece will typically be operated at a speed of 6,000 RPM. As the cutting member 394 is reciprocated, the cutting edge 408 is moved into and along the nasal bone via manipulation of the handpiece assembly. The powered surgical handpiece assembly formed by adapter 10, handpiece 16 and cutting member 394 is advanced longitudinally distally or forwardly and is also moved angularly by the surgeon as the cutting edge 408 is moved into the nasal bone. As shown in dotted lines in FIG. 16, the handpiece assembly is moved angularly or laterally in a pivoting motion so that the cutting edge 408 follows the curved configuration or path for the lateral cut and cuts the nasal bone along a preferred angle. In this manner, a curved or angled lateral cut of a desired length is automatically made in the nasal bone as the surgeon merely guides the cutting element 408 along the preferred curve or angle from the lower or beginning end to an upper or terminal end for the lateral cut. Once the lateral cut has been completed, the osteotome or cutting member 394 is removed from the patient's nose via the incision I. Proper formation of the lateral cut can be confirmed via palpation and/or a remote viewing device where the procedure is performed as a minimally invasive procedure. Once the medial and lateral cuts have been completed, a rasp such as the reciprocating rasp 94, can be introduced at the operative site for shaping or contouring of the nasal bone as described above.

A supraorbital surgical procedure utilizing the rasp or cutting member 194 is illustrated in FIG. 17. The cutting member 194 is coupled with the adapter 10, which is coupled with the handpiece 16, to form a powered surgical handpiece assembly as described above. In addition, a length of tubing Tomita et al is connected to the fitting 202 and to a source of suction. The cutting element 196 of cutting member 194 is introduced between the frontal bone or forehead of the patient's head and overlying anatomical tissue A, the cutting element 196 being introduced through an entry point or incision I disposed at or behind the patient's hairline. Preferably, the incision I is no larger than necessary to receive the cutting element 196 to reduce trauma. The cutting element 196 is moved, via manipulation of the handpiece assembly by the surgeon, distally or forwardly along the patient's frontal bone until the cutting element 196 is positioned at an operative site at the supraorbital bone just behind the patient's eyebrow. Passage of the cutting element 196 from the entry point or incision I to the operative site at the supraorbital bone is facilitated due to the curvature of the shaft 195. The cutting element 196 is introduced between the supraorbital bone and the overlying anatomical tissue A with the cutting element 196 in the specific orientation so that the cutting surface 198 is disposed over and faces an area of the supraorbital bone that is to be reshaped or contoured. Of course, the skin overlying the area of the supraorbital bone that is to be reshaped or contoured can be marked as described above. Proper positioning of the cutting element 196 can be confirmed via palpation since the cutting element 196 can be felt beneath the overlying tissue A as well as by the bulge created in the overlying tissue A due to presence of the cutting element therebeneath.

Once the cutting element 196 is properly located at the location on the supraorbital bone that is to be shaped or contoured, the handpiece 16 is actuated causing reciprocation of cutting element 196. For the rasp 194, the motor of the handpiece will typically be operated at a speed of 5,000 RPM. As the cutting element 196 is reciprocated by the handpiece 16, the handpiece assembly is moved longitudinally and/or laterally by the surgeon in order to correspondingly move the cutting element 196 and thusly abrade and remove some of the supraorbital bone as described above for rasp 94. As the cutting element 196 is reciprocated, suction from the suction source is applied at the operative site via the suction passage 197. In this manner, the supraorbital bone is shaped or contoured in accordance with a desired result while anatomical debris enters the inlet opening of the suction passage 197 and is removed from the operative site via the suction passage 197 and the tubing Tomita et al for withdrawal from the patient's body. The supraorbital bone can be felt through the overlying tissue A when palpated by the surgeon to confirm proper shaping or contouring of the supraorbital bone. Where the supraorbital procedure is performed as a minimally invasive procedure, a remote viewing device can be used to confirm proper shaping or contouring and removal of the proper amount of bone. Once the supraorbital bone has been properly shaped or contoured and the proper amount of bone has been removed therefrom, the rasp 194 is removed from the operative site and is withdrawn through the incision I.

FIG. 18 illustrates an alternative and preferred arrangement for the distal section of the front drive shaft and the nut of the surgical handpiece adapter. FIG. 18 illustrates a front drive shaft 512 having distal section 520 extending distally from distal intermediate section 522. The distal intermediate section 522 is similar to distal intermediate section 22 and has an external thread 535 in threaded engagement with internal thread 541 of nut 538. The distal section 520 includes a cylindrical rearward portion 528, a cylindrical intermediate portion 529 and a cylindrical forward portion 531 extending distally from intermediate portion 529. The rearward portion 528 has an aperture therein communicating with the passage 546 of the front drive shaft and receiving a locking member in the form of a ball 513. The ball 513 has a diametric size capable of permitting protrusion of the ball 513 into the passage 546 while preventing passage of the ball 513 entirely through the aperture. An insert or positioner 515, which is also a ball, is disposed in a notch or recess of the rearward portion 528 and protrudes externally of the front drive shaft 512 to engage an interior surface of nut 538. The insert 515 assists in preventing longitudinal movement of ball 513 and maintaining alignment of ball 513 with its aperture.

The nut 538 is movable longitudinally relative to and along the front drive shaft 512 in response to rotation of the nut 538 as permitted by engagement of threads 535 and 541. When the nut 538 is in a proximal longitudinal position relative to the front drive shaft 512 as shown in FIG. 18, the distal section 520 is in a closed position wherein a cylindrical interior surface of nut 538 engages ball 513 and forces ball 513 in a radially inward direction to protrude through the aperture into the passage 546. The passage 546 is thusly closed so as to prevent passage of a proximal end of a blade or cutting member therethrough. The cylindrical interior surface of nut 538 in engagement with ball 513 in the closed position prevents the ball 513 from moving in a radially outwardly direction. When the nut 538 is moved longitudinally distally relative to the front drive shaft 512 a sufficient distance, the cylindrical interior surface of nut 538 is disengaged from or moved distally of the ball 513 such that the ball 513 is capable of moving in the radially outward direction so that the ball 513 no longer protrudes into the passage 546. The distal section 520 will then be in an open position, with the ball 513 movable in the radially outward direction due to the space or room presented between the front drive shaft and the nut when a sloping interior surface of the nut is aligned with the ball 513. The passage 546 will then be in an open position allowing a proximal end of a blade or cutting member to pass therethrough. The balls 513 and 515, being spherical, facilitate longitudinal movement of the nut 538 relative to the front drive shaft 512.

The arrangement depicted in FIG. 18 is adapted to be used with a cutting member having an external annular groove thereon for being engaged and disengaged with the ball 513 to selectively lock and unlock the cutting member to the front drive shaft. FIG. 19 illustrates a preferred surgical rasp 694 adapted for use with an adapter having front drive shaft 512 and nut 538. Rasp 694 is the same as rasp 94 except that shaft 695 for rasp 694 has an external annular or circumferential groove 617 formed thereon. The groove 617 is disposed on shaft 695 at a location aligned with ball 513 and its aperture when the shaft 695 is fully inserted in the passage 546 of the front drive shaft 512. The shaft 695 is insertable in the passage 546 with the nut 538 in the distal longitudinal position, the ball 513 being moved in the radially outward direction by the shaft 695 to open the passage 546 as it is inserted therein. The ball 513 is thusly moved by the shaft 695 out of the passage 546 so that the distal section 520 is in the open position allowing the shaft 695 to be fully inserted in the now open passage 546. Once the shaft 695 is fully inserted in passage 546, the nut 538 is rotated or turned to move it to the proximal longitudinal position. As a result thereof, the ball 513 is moved in the radially inward direction causing it to protrude through the aperture and into the groove 617 aligned therewith. The distal section 520 will then be in the closed position with the ball 513 received in the groove 617 and closing the passage 546 to movement of the shaft 695 therethrough. Since the ball 513 is captured it is prevented from moving longitudinally, and the rasp 694 is locked to the front drive shaft 512. The rasp 694 is removable or disengageable from the front drive shaft by moving the nut 538 to the distal longitudinal position allowing the shaft 695 to be withdrawn from passage 546. As the shaft 695 is withdrawn, it moves the ball 513 in the radially outward direction so that the distal section 520 is in the open position.

Actuation of the powered surgical handpiece can be controlled so that the motor thereof is turned or rotated at a desired speed in accordance with the speed of reciprocation desired for the cutting element. The adapter according to the present invention permits the rotary output of the powered surgical handpiece to be selectively converted into reciprocating motion in order to reciprocatively drive a blade or cutting member. Although the adapter of the subject invention is designed for use with the XPS™ StraightShot handpiece to allow the XPS™ StraightShot handpiece to be used to drive both rotary and reciprocative blades or cutting members, it should be appreciated that the adapter can be used with various powered surgical handpieces having rotatable drive shafts. Accordingly, the proximal end of the rear drive shaft of the adapter can be designed in various ways allowing the rear drive shaft to be mechanically coupled to the drive shaft of the handpiece. The adapter can be used to reciprocatively drive various types of reciprocative blades or cutting members, and the adapter and a blade or cutting member coupled therewith forms a handpiece adapter assembly. The adapter can be used to drive reciprocative blades at various speeds to perform various cutting functions in anatomical tissue including bone. The adapter can be designed with a particular stroke and a plurality of adapters can be provided each having a different stroke. The adapter can be provided with an alignment member to ensure coupling of a blade or cutting member therewith in a specific orientation. The adapter can be designed for mechanical coupling with the drive shaft of the handpiece with the blade or cutting member that is coupled with the adapter disposed in the specific orientation relative to the handpiece. In this manner, the blade or cutting member is in the proper orientation for use thereof when the handpiece is grasped or held by the surgeon in the normal manner. The adapter can be used in a powered surgical handpiece assembly to reciprocatively drive various blades or cutting members thereof in surgical procedures that are performed minimally invasively. The adapter can be designed for reuse in conjunction with a reusable handpiece and disposable blades or cutting members.

The rasps according to the present invention greatly facilitate the performance of surgical procedures since anatomical debris is removed from operative sites via the rasps themselves. The suction passages of the rasps have inlet openings disposed along cutting surfaces of the rasps and are thusly disposed at the source of the anatomical debris. The rasps can be provided with a longitudinal curve or bend particularly useful in specific procedures to access internal operative sites from entry points or incisions disposed at locations remote from the operative sites. The rasps can be provided with cutting elements of varying sharpness or coarseness. A plurality or series of rasps can be provided each having a different sharpness or coarseness. The rasps can be coupled with various adapters to form various handpiece adapter assemblies. The rasps can be coupled with various handpieces via various adapters to form various powered surgical handpiece assemblies.

The osteotomes greatly reduce the amount of time needed to perform various surgical procedures, particularly facial procedures such as rhinoplasty. When used in a powered surgical handpiece assembly, the osteotomes allowed medial and lateral cuts to be formed in the nasal bone automatically, with the surgeon having only to guide the cutting elements of the osteotomes. The osteotomes can be longitudinally straight for formation of longitudinally straight cuts or longitudinally curved or angled for formation of longitudinally curved or angled cuts. The blunt distal tips of the osteotomes lead and guide the cutting elements of the osteotomes to operatives sties at which the osteotomes are to be used and protect surrounding anatomical tissue from unwanted contact with the cutting edges. The osteotomes can be coupled with various adapters to form various handpiece adapter assemblies. The osteotomes can be coupled with various handpieces via various adapters to form various powered surgical handpiece assemblies.

The blades or cutting members can be provided with structure cooperable with structure of the adapter to ensure that the blades or cutting members are coupled to the adapter and, therefore, the handpiece, in the proper orientation for use.

Inasmuch as the present invention is subject to various modification, and changes in detail, it should be appreciated that the preferred embodiments described herein should be considered as illustrative only and should not be taken in a limiting sense.

What is claimed is:

1. A surgical suction rasp for being reciprocatively driven by a reciprocating driver to shape anatomical tissue at an operative site in a patient's body comprising an elongate member having a proximal end for being removably coupled to a reciprocating driver and having a distal end for being disposed at an operative site, a cutting element at said distal end comprising a tissue cutting surface and a surface opposite said tissue cutting surface, a suction passage having an inlet along said tissue cutting surface and having an outlet disposed proximally of said inlet, said suction passage comprising a portion extending through said cutting element from said inlet to an exit along said surface opposite said tissue cutting surface and comprising another portion extending externally alongside said elongate member from said exit toward said outlet, said tissue cutting surface being configured to abrade and thusly cut anatomical tissue at the operative site when said tissue cutting surface is positioned in contact with the anatomical tissue while said elongate member is reciprocated by the reciprocating driver, said outlet of said suction passage being adapted for connection to a source of suction whereby anatomical debris is removed from the operative site through said suction passage for withdrawal from the patient's body.

2. A surgical suction rasp as recited in claim 1 wherein said tissue cutting surface comprises a planar surface having a plurality of sharp ridges for abrading bone.

3. A surgical suction rasp as recited in claim 2 wherein said ridges are formed by a plurality of diamond shaped protuberances on said planar surface.

4. A surgical suction rasp as recited in claim 2 wherein said surface opposite said tissue cutting surface is curved.

5. A surgical suction rasp as recited in claim 4 wherein said surface opposite said tissue cutting surface extends proximally at an angle to said tissue cutting surface.

6. A surgical suction rasp as recited in claim 2 wherein said tissue cutting surface has a perimeter of oblong configuration and said surface opposite said tissue cutting surface is joined to said perimeter.

7. A surgical suction rasp as recited in claim 6 wherein said perimeter is defined by a rectangle with rounded corners.

8. A surgical suction rasp as recited in claim 2 wherein said inlet comprises a hole and said ridges are disposed on the entire area of said tissue cutting surface except for said hole.

9. A surgical suction rasp as recited in claim 1 wherein said elongate member has a central longitudinal axis and said tissue cutting surface is laterally offset from said central longitudinal axis.

10. A surgical suction rasp as recited in claim 9 wherein said central longitudinal axis is longitudinally straight and said tissue cutting surface is parallel to said central longitudinal axis.

11. A surgical suction rasp as recited in claim 9 wherein said central longitudinal axis has a longitudinal curvature.

12. A surgical suction rasp as recited in claim 11 wherein said longitudinal curvature corresponds to the natural curvature of a human frontal bone.

13. A surgical suction rasp as recited in claim 11 wherein said another portion of said suction passage follows said longitudinal curvature.

14. A surgical suction rasp as recited in claim 1 wherein said elongate member has a central longitudinal axis and said portion of said suction passage extends entirely through said cutting element at an angle to said central longitudinal axis.

15. A surgical suction rasp as recited in claim 14 wherein said outlet is disposed proximally of said distal end of said elongate member.

16. A surgical suction rasp as recited in claim 15 wherein said another portion of said suction passage includes a tube.

17. A surgical suction rasp as recited in claim 16 wherein said tube has a proximal end terminating at said outlet and said proximal said of the tube is angled outwardly from said elongate member.

18. A surgical suction rasp as recited in claim 17 wherein said tube has a distal end terminating at said tissue cutting surface.

19. A surgical suction rasp as recited in claim 1 wherein said cutting element has a height between said tissue cutting surface and said surface opposite said tissue cutting surface, and said height increases in a proximal direction from a distal edge of said tissue cutting surface.

20. A surgical suction rasp as recited in claim 1 said portion of said suction passage extends angularly, proximally from said inlet at an angle of 30 degrees to said tissue cutting surface.

21. A surgical suction rasp as recited in claim 1 wherein said outlet comprises a fitting for connection with a source of suction.

22. A surgical suction rasp as recited in claim 1 wherein said elongate member is solid.

23. A handpiece adapter assembly for a powered surgical handpiece comprising a handpiece adapter for being removably coupled with a rotatable drive shaft of a powered surgical handpiece and having a front drive shaft and a motion converting mechanism by which rotary motion of the drive shaft of the handpiece is converted to reciprocating motion of said front drive shaft; and a suction rasp removably coupled to said front drive shaft for being reciprocatively driven thereby and including an elongate member having a proximal end removably coupled to said front drive shaft, a distal end for being disposed at an operative site in a patient's body, a tissue cutting surface at said distal end and a suction passage having an inlet along said tissue cutting surface and having an outlet disposed proximally of said inlet, said suction rasp including a cutting element at said distal end of said elongate member comprising said tissue cutting surface and a surface opposite said tissue cutting surface, said suction passage comprising a portion extending through said cutting element from said inlet to an exit along said surface opposite said tissue cutting surface and comprising another portion extending externally alongside said elongate member from said exit toward said outlet, said tissue cutting surface having a configuration to abrade and thusly cut anatomical tissue at the operative site when said tissue cutting surface is positioned in contact with the anatomical tissue while said elongate member is reciprocated by said front drive shaft, said outlet of said suction passage being adapted for connection to a source of suction whereby anatomical debris is removed from the operative site through said suction passage for withdrawal from the patient's body.

24. A powered surgical handpiece assembly comprising a powered surgical handpiece having a rotatable drive shaft;

a handpiece adapter removably coupled with said rotatable drive shaft and having a front drive shaft and a motion converting mechanism by which rotary motion of said rotatable drive shaft is converted to reciprocating motion of said front drive shaft; and a suction rasp removably coupled to said front drive shaft for being reciprocatively driven thereby and including an elongate member having a proximal end removably coupled to said front drive shaft, a distal end for being disposed at an operative site in a patient's body, a tissue cutting surface at said distal end and a suction passage having an inlet along said tissue cutting surface and having an outlet disposed proximally of said inlet, said suction rasp including a cutting element at said distal end of said elongate member comprising said tissue cutting surface and a surface opposite said tissue cutting surface, said suction passage comprising a portion extending through said cutting element from said inlet to an exit along said surface opposite said tissue cutting surface and comprising another portion extending externally alongside said elongate member from said exit toward said outlet, said tissue cutting surface having a configuration to abrade and thusly cut anatomical tissue at the operative site when said tissue cutting surface is positioned in contact with the anatomical tissue while said elongate member is reciprocated by said front drive shaft, said outlet of said suction passage being adapted for connection to a source of suction whereby anatomical debris is removed from the operative site through said suction passage for withdrawal from the patient's body.

\* \* \* \* \*